(12) United States Patent
Ohsawa et al.

(10) Patent No.: US 6,416,928 B1
(45) Date of Patent: Jul. 9, 2002

(54) ONIUM SALTS, PHOTOACID GENERATORS, RESIST COMPOSITIONS, AND PATTERNING PROCESS

(75) Inventors: Youichi Ohsawa; Jun Watanabe; Satoshi Watanabe; Shigehiro Nagura, all of Nakakubiki-gun (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 3 days.

(21) Appl. No.: 09/680,491

(22) Filed: Oct. 5, 2000

(30) Foreign Application Priority Data

Oct. 6, 1999 (JP) ............................. 11-285143

(51) Int. Cl.$^7$ ....................... G03F 7/004; C07C 315/00; C07C 331/00; C07C 17/00
(52) U.S. Cl. ................... 430/270.1; 430/326; 430/914; 430/921; 522/31; 568/34; 568/38; 568/50; 568/58; 568/77; 570/101
(58) Field of Search ............................. 430/270.1, 326, 430/914, 921; 568/34, 77, 38, 50, 58; 570/101; 522/31

(56) References Cited

U.S. PATENT DOCUMENTS

| | | | |
|---|---|---|---|
| 5,191,124 A | * 3/1993 | Schwalm et al. ............. 568/18 |
| 5,492,793 A | 2/1996 | Breyta et al. |
| 5,558,971 A | 9/1996 | Urano et al. |
| 5,558,976 A | 9/1996 | Urano et al. |
| 5,625,020 A | 4/1997 | Breyta et al. |
| 5,633,409 A | * 5/1997 | Watanabe et al. ............. 568/49 |
| 5,837,420 A | 11/1998 | Aoai et al. |

FOREIGN PATENT DOCUMENTS

| | | |
|---|---|---|
| JP | 6-148889 | 5/1994 |
| JP | 6-199770 | 7/1994 |
| JP | 6-266112 | 9/1994 |
| JP | 8-123032 | 5/1996 |
| JP | 9-244234 | 9/1997 |
| JP | 9-258435 | 10/1997 |
| JP | 11-72921 | 3/1999 |

OTHER PUBLICATIONS

English Abstract for JP 11–72921.
English Abstract for JP 6–148889.
English Abstract for JP 6–199770.
English Abstract for JP 9–258435.

* cited by examiner

Primary Examiner—Rosemary Ashton
(74) Attorney, Agent, or Firm—Millen, White, Zelano & Branigan, P.C.

(57) ABSTRACT

Onium salts of substituted phenylmethylbenzene-sulfonate anions with iodonium or sulfonium cations are novel. A chemically amplified resist composition comprising the onium salt as a photoacid generator is suited for microfabrication, especially by deep UV lithography because of many advantages including improved resolution, minimized line width variation or shape degradation even on long-term PED, minimized defect after coating, development and peeling, and improved pattern profile after development.

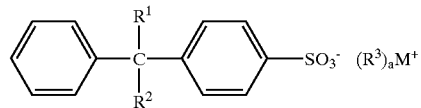

18 Claims, No Drawings

ONIUM SALTS, PHOTOACID GENERATORS, RESIST COMPOSITIONS, AND PATTERNING PROCESS

This invention relates to novel onium salts, photoacid generators for resist compositions, resist compositions comprising the photoacid generators, and a patterning process using the same. The resist compositions, especially chemical amplification type resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of efforts are currently being made to achieve a finer pattern rule in the drive for higher integration and operating speeds in LSI devices, deep-ultraviolet lithography is thought to hold particular promise as the next generation in microfabrication technology.

One technology that has attracted a good deal of attention recently utilizes as the deep UV light source a high-intensity KrF excimer laser, especially an ArF excimer laser featuring a shorter wavelength. There is a desire to have a microfabrication technique of finer definition by combining exposure light of shorter wavelength with a resist material having a higher resolution.

In this regard, the recently developed, acid-catalyzed, chemical amplification type resist materials are expected to comply with the deep UV lithography because of their many advantages including high sensitivity, resolution and dry etching resistance. The chemical amplification type resist materials include positive working materials that leave the unexposed areas with the exposed areas removed and negative working materials that leave the exposed areas with the unexposed areas removed.

In chemical amplification type, positive working, resist compositions to be developed with alkaline developers, an alkali-soluble phenol or a resin and/or compound in which carboxylic acid is partially or entirely protected with acid-labile protective groups (acid labile groups) is catalytically decomposed by an acid which is generated upon exposure, to thereby generate the phenol or carboxylic acid in the exposed area which is removed by an alkaline developer. Also, in similar negative working resist compositions, an alkali-soluble phenol or a resin and/or compound having carboxylic acid and a compound (crosslinking agent) capable of bonding or crosslinking the resin or compound under the action of an acid are crosslinked with an acid which is generated upon exposure whereby the exposed area is converted to be insoluble in an alkaline developer and the unexposed area is removed by the alkaline developer.

On use of the chemical amplification type, positive working, resist compositions, a resist film is formed by dissolving a resin having acid labile groups as a binder and a compound capable of generating an acid upon exposure to radiation (to be referred to as photoacid generator) in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemical amplification type, positive working, resist compositions adapted for KrF excimer lasers generally use a phenolic resin, for example, polyhydroxystyrene in which some or all of the hydrogen atoms of phenolic hydroxyl groups are protected with acid labile protective groups. Onium salts such as iodonium salts and sulfonium salts, bissulfonyldiazomethane compounds, and N-sulfonyloxyimide compounds are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Onium salts as shown below are advantageously used as the photoacid generator in chemical amplification type resist compositions, especially chemical amplification type, positive working, resist compositions adapted for KrF excimer lasers because they provide a high sensitivity and resolution and are free from storage instability as found with the N-sulfonyloxyimide photoacid generators.

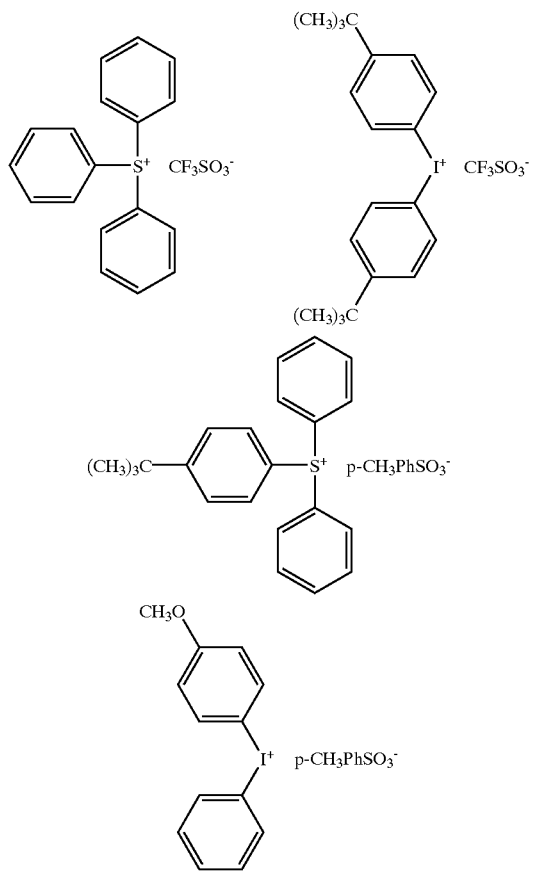

Since a finer pattern size is required, even the use such photoacid generators gives rise to many problems including low resolution, low environmental stability, and the formation of insoluble or difficultly soluble foreign matter upon development with an alkaline developer or removal of the resist with a solvent.

Of these problems, improvements in resolution are made by introducing into a resin acid labile groups which are more prone to scission by an acid, or adding a basic compound, or modifying processing conditions.

It is known from JP-A 8-123032 to use two or more photoacid generators in a resist material. JP-A 11-72921 discloses the use of a radiation-sensitive acid generator comprising in admixture a compound which generates a sulfonic acid having at least three fluorine atoms upon exposure to radiation and a compound which generates a fluorine atom-free sulfonic acid upon exposure to radiation, thereby improving resolution without inviting nano-edge roughness and film surface roughening. However, we empirically found that these resist compositions are unsatisfactory in resolution and in the effect of eliminating the foreign matter on the pattern upon development.

For the purpose of improving the resolution upon microfabrication, JP-A 6-148889 discloses a positive photosensitive composition comprising a polyfunctional enol ether compound and an alkali-soluble resin as typified by polyhydroxystyrene, which are thermally crosslinked on a substrate, followed by exposure to radiation and PEB to provide a desired pattern. JP-A 6-266112 discloses a photosensitive resist composition comprising a photosensitive acid generator and a polymer composed of hydroxystyrene and an acrylate and/or methacrylate. These compositions are unsatisfactory in resolution and pattern profile. Substantial sliming upon post-exposure delay (PED) is also a problem.

The environmental stability is generally divided into two categories. One environmental stability is related to the deactivation of a photo-generated acid by an air-borne base above the resist film or a base beneath the resist film and on the substrate. This phenomenon is often seen when a photoacid generator capable of generating an acid having a high acid strength is used. It is expected that this problem is solved by introducing into the resin acid labile groups which are more easy to cleavage by acid or by lowering or weakening the acid strength of the photo-generated acid. The other environmental stability is that when the period from exposure to post-exposure baking (PEB) is prolonged, which is known as post-exposure delay (PED), the photogenerated acid diffuses in the resist film so that acid deactivation may occur when the acid labile groups are less susceptible to cleavage and acid decomposition may take place when the acid labile groups are susceptible to cleavage, often inviting a change of the pattern profile in either case. For example, this invites a sliming of the line width in the unexposed area in the case of chemical amplification type, positive working, resist compositions having acid labile groups, typically acetal groups.

As mentioned above, for achieving a high resolution, the resin should have introduced therein acid labile groups which are more easy to cleavage, and the photoacid generator should desirably generate a less diffusible acid. The less diffusible acids under investigation are alkylsulfonic acids such as 10-camphorsulfonic acid. The alkylsulfonic acids, however, are weak in acid strength as compared with the conventionally used fluorinated alkylsulfonic acids and arylsulfonic acids, and such low acid strength must be compensated for by the quantity of acid. In order that a more quantity of acid be generated, the exposure time must be increased, often leading to poor productivity.

Addressing this problem, JP-A 6-199770, 9-244234 and 9-258435 disclose resist compositions using photoacid generators in the form of arylsulfonic acids having an alkyl, carbonyl or carboxylate group introduced therein.

However, we empirically found that the direct introduction of a carbonyl or carboxylate group into a benzene ring is effective for suppressing the diffusion of the generated acid, but undesirably increases the light absorption near 248 nm of the photoacid generator and that the introduction of an alkyl group can undesirably leave defect (residue) upon development.

With respect to the foreign matter left upon alkali development and/or removal of the resist film with a solvent, a variety of factors including photo-decomposed products of the photoacid generator, non-decomposed compound (that is the photoacid generator as such) and low soluble resin are considered, and none of these factors have been identified responsible. However, the defect is probably correlated to the solubility or affinity of the photoacid generator in the developer (aqueous solution) or remover solvent and the solubility or affinity thereof in the resin.

The photoacid generator in resist material is required to meet a fully high solubility in (or compatibility with) a resist solvent and a resin, good storage stability, non-toxicity, effective coating, a well-defined pattern profile, PED stability, and no foreign matter left during pattern formation after development and upon resist removal. The conventional photoacid generators, especially those photoacid generators capable of generating alkylsulfonic acids and arylsulfonic acids do not meet all of these requirements.

As the pattern of integrated circuits becomes finer in these days, a higher resolution is, of course, required, and the problems of line width variation by PED and defect after development and resist removal become more serious.

SUMMARY OF THE INVENTION

An object of the invention is to provide a novel onium salt for use in a resist composition, especially of the chemical amplification type, such that the resist composition ensures a high resolution and a well-defined pattern profile after development and minimizes the defect (residue) left after development and resist removal. Another object of the invention is to provide a photoacid generator for resist compositions, a resist composition comprising the photoacid generator, and a patterning process using the same.

We have found that by using an onium salt of the general formula (1), especially a sulfonium salt of the general formula (1a) or (1a') or an iodonium salt of the general formula (1b), to be defined below, as the photoacid generator in a resist composition, there are achieved a number of advantages including storage stability, effective coating, minimized line width variation or shape degradation during long-term PED, minimized defect left after coating, development and resist removal, a well-defined pattern profile after development, and a high resolution enough for microfabrication, especially by deep UV lithography.

When the onium salt of formula (1) is used in a chemical amplification type resist composition as the photoacid generator, a resist image featuring a high resolution and a wide range of focal depth is obtainable due to the low diffusing effect of sulfonic acid anions. At the same time, the degradation of a pattern profile by PED is minimized, and the defect left after alkali development and resist removal is minimized due to the polarity of the sulfonium salt or iodonium salt.

Therefore, the invention provides onium salts, photoacid generators, resist compositions and a patterning process as defined below.

In a first aspect, the invention provides an onium salt of the following general formula (1).

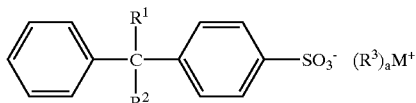

(1)

Herein $R^1$ is hydrogen or a straight, branched or cyclic alkyl group of 1 to 6 carbon atoms, $R^2$ is hydrogen, a straight, branched or cyclic alkyl group of 1 to 6 carbon atoms or phenyl group, $R^3$ which may be the same or different is a substituted or unsubstituted, straight, branched or cyclic alkyl group of 1 to 10 carbon atoms or substituted or unsubstituted aryl group of 6 to 14 carbon atoms, M is a sulfur or iodine atom, and "a" is equal to 3 when M is sulfur and equal to 2 when M is iodine.

A sulfonium salt of the following general formula (1a) is also provided:

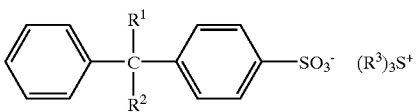

(1a)

wherein $R^1$, $R^2$ and $R^3$ are as defined above.

A sulfonium salt of the following general formula (1a') is also provided:

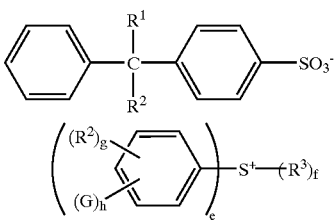

(1a')

wherein $R^1$, $R^2$ and $R^3$ are as defined above, G is an acid labile group having an oxygen atom attached thereto or $R^2O$— or $(R^2)_2N$—, g is an integer of 0 to 4, h is an integer of 1 to 5, g+h=5, e is an integer of 1 to 3, f is an integer of 0 to 2, and e+f=3.

Preferably, the acid labile group is selected from the group consisting of tert-butoxy group, tert-amyloxy group, tert-butoxycarbonyloxy group, tert-butoxycarbonylmethyloxy group, 1-ethoxyethoxy group, tetrahydropyranyloxy group, tetrahydrofuranyloxy group, trimethylsilyloxy group and 1-ethylcyclopentyloxy group.

A iodonium salt of the following general formula (1b) is also provided.

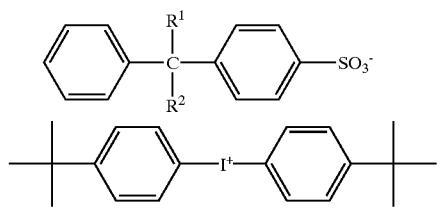

(1b)

wherein $R^1$ and $R^2$ are as defined above.

In a second aspect, the invention provides a photoacid generator for a chemical amplification type resist composition comprising the onium salt defined above.

In a third aspect, the invention provides a chemical amplification type resist composition comprising (A) a resin which changes its solubility in an alkaline developer under the action of an acid, and (B) the photoacid generator of the second aspect which generates an acid upon exposure to radiation.

Also provided is a chemical amplification type resist composition comprising (A) a resin which changes its solubility in an alkaline developer under the action of an acid, (B) the photoacid generator of the second aspect which generates an acid upon exposure to radiation, and (C) a compound capable of generating an acid upon exposure to radiation, other than component (B).

Preferably, the resin (A) has such substituent groups having C—O—C linkages that the solubility in an alkaline developer changes as a result of cleavage of the C—O—C linkages under the action of an acid.

Also preferably, the resin (A) is a polymer containing phenolic hydroxyl groups in which hydrogen atoms of the phenolic hydroxyl groups are replaced by acid labile groups of at least one type in a proportion of more than 0 mol % to 80 mol %, on the average, of the entire hydrogen atoms of the phenolic hydroxyl groups, said polymer having a weight average molecular weight of 3,000 to 100,000.

Also preferably, the resin (A) is a polymer comprising recurring units represented by the following general formula (2a):

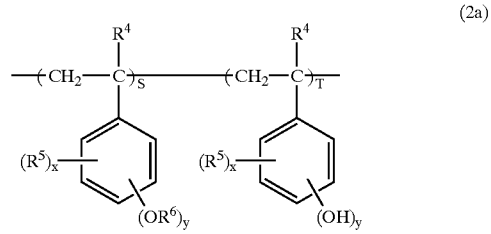

(2a)

wherein the units having the acid labile groups are present in a proportion of more than 0 mol % to 80 mol %, on the average, based on the entire polymer, and the polymer has a weight average molecular weight of 3,000 to 100,000.

Herein, $R^4$ is hydrogen or methyl, $R^5$ is a straight, branched or cyclic alkyl group of 1 to 8 carbon atoms, $R^6$ is an acid labile group, $R^6$ groups may be the same or different when y is at least 2, x is 0 or a positive integer, satisfying x+y≦5, and S and T are positive integers, satisfying 0<S/(S+T)≦0.8.

Further preferably, the resin (A) is a polymer comprising recurring units represented by the following general formula (2a'), wherein the units of acrylate and methacrylate are contained in the polymer in a proportion of more than 0 mol % to 50 mol % on the average, the units having the acid labile groups are present in a proportion of more than 0 mol % to 80 mol %, on the average, based on the entire polymer, and the polymer has a weight average molecular weight of 3,000 to 100,000.

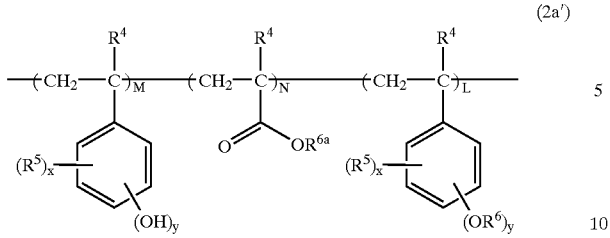

(2a')

Herein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, $R^{6a}$ being at least partially an acid labile group, x is 0 or a positive integer, y is a positive integer, satisfying $x+y \leq 5$, the $R^6$ groups may be the same or different when y is at least 2, M and N are positive integers, L is 0 or a positive integer, satisfying $0<N/(M+N) \leq 0.5$ and $0<(N+L)/(M+N+L) \leq 0.8$.

Further preferably, the resin (A) is the polymer of formula (2a) or (2a') in which the hydrogen atoms of the remaining phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3a) or (3b).

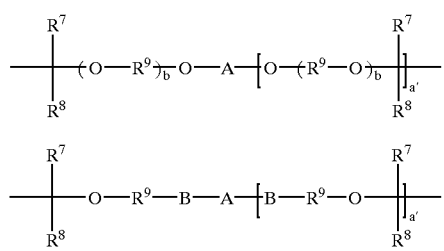

(3a)

(3b)

Herein each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring, $R^9$ is a straight, branched or cyclic alkylene group of 1 to 10 carbon atoms, letter a' is an integer of 1 to 7, preferably 1 to 3, letter b is 0 or an integer of 1 to 10, A is an (a'+1)-valent aliphatic or alicyclic saturated hydrocarbon group, aromatic hydrocarbon group or heterocyclic group of 1 to 50 carbon atoms, which may be separated by a hetero atom and in which some of the hydrogen atoms attached to carbon atoms may be replaced by hydroxyl, carboxyl, carbonyl or halogen, B is —CO—O—, —NHCO—O— or —NHCONH—.

The acid labile groups are preferably groups of the following general formulae (4) to (7), tertiary alkyl groups of 4 to 20 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

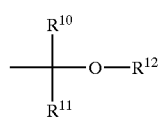

(4)

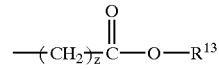

(5)

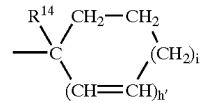

(6)

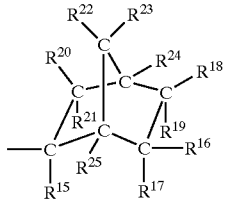

(7)

Herein $R^{10}$ and $R^{11}$ are independently hydrogen or straight, branched or cyclic alkyl groups of 1 to 18 carbon atoms, $R^{12}$ is a monovalent hydrocarbon group of 1 to 18 carbon atoms which may have a hetero atom, or $R^{10}$ and $R^{11}$, $R^{10}$ and $R^{12}$, or $R^{11}$ and $R^{12}$, taken together, may form a ring, with the proviso that each of $R^{10}$, $R^{11}$ and $R^{12}$ is a straight or branched alkylene group of 1 to 18 carbon atoms when they form a ring, $R^{13}$ is a tertiary alkyl group of 4 to 20 carbon atoms, a trialkylsilyl group whose alkyl groups each have 1 to 6 carbon atoms, an oxoalkyl group of 4 to 20 carbon atoms or a group of formula (4), and letter z is an integer of 0 to 6, $R^{14}$ is a straight, branched or cyclic alkyl group of 1 to 8 carbon atoms or substituted or unsubstituted aryl group of 6 to 20 carbon atoms, h' is equal to 0 or 1, i is equal to 0, 1, 2 or 3, satisfying 2h'+i=2 or 3, $R^{15}$ is a straight, branched or cyclic alkyl group of 1 to 8 carbon atoms or substituted or unsubstituted aryl group of 6 to 20 carbon atoms, $R^{16}$ to $R^{25}$ are independently hydrogen or monovalent hydrocarbon groups of 1 to 15 carbon atoms which may contain a hetero atom, or $R^{16}$ to $R^{25}$, taken together, may form a ring, with the proviso that they are divalent hydrocarbon groups of 1 to 15 carbon atoms which may contain a hetero atom when they form a ring, or two of $R^{16}$ to $R^{25}$ which are attached to adjacent carbon atoms may directly bond together to form a double bond. More preferably, the resin (A) is of the formula (2a') wherein the acid labile group represented by $R^{6a}$ is a tertiary alkyl group of 4 to 20 carbon atoms, an aryl-substituted alkyl group of 7 to 20 carbon atoms, an oxoalkyl group of 4 to 20 carbon atoms or a group of formula (4).

The resist composition may further contain (D) a basic compound, (E) a carboxyl group-containing compound, and/or a solvent which is a propylene glycol alkyl ether acetate, an alkyl lactate or a mixture thereof.

Also contemplated herein is a process for forming a pattern, comprising the steps of applying the above-defined resist composition onto a substrate to form a coating; heat treating the coating and exposing the coating to high energy radiation with a wavelength of up to 300 nm or electron beam through a photo-mask; optionally heat treating the exposed coating, and developing the coating with a developer.

DESCRIPTION OF THE PREFERRED EMBODIMENT

Onium Salt

In the first aspect, the invention provides a novel onium salt having a substituted phenylmethylbenzenesulfonate anion of the following general formula (1).

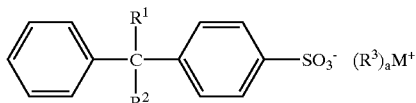

(1)

Herein $R^1$ is hydrogen or a straight, branched or cyclic alkyl group of 1 to 6 carbon atoms. $R^2$ is hydrogen, a straight, branched or cyclic alkyl group of 1 to 6 carbon atoms or phenyl group. $R^3$ which may be the same or different is hydrogen or a substituted or unsubstituted, straight, branched or cyclic alkyl group of 1 to 10 carbon atoms or substituted or unsubstituted aryl group of 6 to 14 carbon atoms. M is a sulfur or iodine atom, and "a" is equal to 3 when M is sulfur and equal to 2 when M is iodine.

Specifically, the invention provides a novel sulfonium salt having a substituted phenylmethylbenzenesulfonate anion of the following general formula (1a) or (1a').

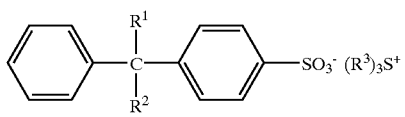

(1a)

Herein $R^1$, $R^2$ and $R^3$ are as defined above.

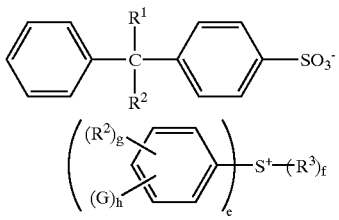

(1a')

Herein $R^1$, $R^2$ and $R^3$ are as defined above. G is an acid labile group having an oxygen atom attached thereto or $R^2O$— or $(R^2)_2N$—, g is an integer of 0 to 4, h is an integer of 1 to 5, g+h=5, e is an integer of 1 to 3, f is an integer of 0 to 2, and e+f=3.

Specifically, the invention also provides a novel iodonium salt having a substituted phenylmethylbenzenesulfonate anion of the following general formula (1b).

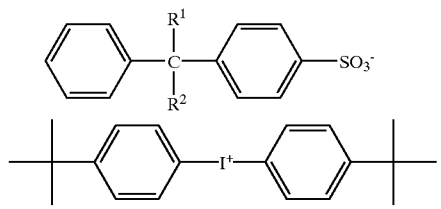

(1b)

Herein $R^1$ and $R^2$ are as defined above.

In formulae (1), (1a), (1a') and (1b), $R^1$ stands for hydrogen or straight, branched or cyclic alkyl groups of 1 to 6 carbon atoms, and the $R^1$ groups may be the same or different. Illustrative, non-limiting, examples of the straight, branched or cyclic alkyl groups include methyl, ethyl, n-propyl, sec-propyl, n-butyl, sec-butyl, iso-butyl, tert-butyl, n-pentyl, sec-pentyl, cyclopentyl, n-hexyl, and cyclohexyl.

In formulae (1), (1a), (1a') and (1b), $R^2$ stands for hydrogen, straight, branched or cyclic alkyl groups of 1 to 6 carbon atoms or phenyl groups, and the $R^2$ groups may be the same or different. Illustrative, non-limiting, examples of the straight, branched or cyclic alkyl groups include methyl, ethyl, n-propyl, sec-propyl, n-butyl, sec-butyl, iso-butyl, tert-butyl, n-pentyl, sec-pentyl, cyclopentyl, n-hexyl, and cyclohexyl.

Alternatively, $R^1$ and $R^2$ may form a cyclic structure of 4 to 7 carbon atoms, such as cycloalkyl, with the carbon atom to which they are attached.

In formulae (1), (1a), (1a') and (1b), $R^3$ stands for substituted or unsubstituted, straight, branched or cyclic alkyl groups of 1 to 10 carbon atoms or substituted or unsubstituted aryl groups of 6 to 14 carbon atoms, and the $R^3$ groups may be the same or different. Exemplary of $R^3$ are straight, branched or cyclic alkyl groups such as methyl, ethyl, n-propyl, sec-propyl, n-butyl, sec-butyl, iso-butyl, tert-butyl, n-pentyl, sec-pentyl, cyclopentyl, n-hexyl, and cyclohexyl; substituted alkyl groups, for example, oxo- and hydroxy-substituted alkyl groups such as 2-oxopropyl, 2-oxocyclopentyl, 2-oxocyclohexyl, 2-hydroxycyclopentyl and 2-hydroxycyclohexyl; and unsubstituted aryl groups and alkyl-, alkoxy- and alkylamino-substituted aryl groups such as phenyl, 4-methylphenyl, 4-ethylphenyl, 4-methoxyphenyl, 4-tert-butylphenyl, 4-tert-butoxyphenyl, 4-cyclohexylphenyl, 4-cyclohexyloxyphenyl, 2,4-dimethylphenyl, 2,4,6-trimethylphenyl, 2,4,6-triisopropylphenyl, 3,4-bis(tert-butoxy)phenyl, 4-dimethylaminophenyl, 1-naphthyl and 2-naphthyl, though not limited thereto. In formula (1), M is a sulfur or iodine atom, and "a" is equal to 3 when M is sulfur and equal to 2 when M is iodine.

In formula (1a'), G is an acid labile group having an oxygen atom attached thereto (represented by —OG' wherein G' is an acid labile group) or an alkoxy group: $R^2O$— or a group: $(R^2)_2N$— wherein $R^2$ is as defined above. The acid labile group having an oxygen atom attached thereto are exemplified by the same acid labile groups of a resin of component (A) described later, although not limited thereto. Preferably, the acid labile group is selected from the group consisting of tert-butoxy group, tert-amyloxy group, tert-butoxycarbonyloxy group, tert-butoxycarbonylmethyloxy group, 1-ethoxyethoxy group, tetrahydropyranyloxy group, tetrahydrofuranyloxy group, trimethylsilyloxy group and 1-ethylcyclopentyloxy group.

The onium salts according to the invention are salts of substituted phenylmethylbenzenesulfonate anions with iodonium or sulfonium cations. Exemplary anions include a 4-phenylmethylbenzenesulfonate anion, 4-(diphenylmethyl)benzenesulfonate anion, and 4-(1'-methyl-1'-phenyl)ethylbenzenesulfonate anion.

Exemplary iodonium cations include diphenyliodonium, bis(4-tert-butylphenyl)iodonium, 4-methoxyphenylphenyliodonium, 4-ethoxyphenylphenyliodonium, and 4-tert-butoxyphenylphenyliodonium, with the diphenyliodonium and bis(4-tert-butoxyphenyl)iodonium are preferred.

Exemplary sulfonium cations include triphenylsulfonium, 4-hydroxyphenyldiphenylsulfonium, (4-tert-butylphenyl)diphenylsulfonium, bis(4-tert-butylphenyl)phenylsulfonium, tris(4-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tertbutoxycarbonylmethyloxyphenyl)diphenylsulfonium, tris (4-tert-butoxycarbonylmethyloxyphenyl)sulfonium, (4-tert-butoxyphenyl)bis(4-dimethylaminophenyl)sulfonium, tris (4-dimethylaminophenyl)sulfonium, 2-naphthyldiphenylsulfonium, dimethyl-2-naphthylsulfonium, 4-hydroxyphenyldimethylsulfonium, 4-methoxyphenyldimethyl-sulfonium, dimethylphenylsulfonium, diphenylmethylsulfonium, trimethylsulfonium, 2-oxocyclohexylcyclohexylmethylsulfonium, 2-oxocyclohexyl-methyl-phenylsulfonium, 2-oxocyclopentyl-methyl-phenylsulfonium, 2-oxocyclopropyl-methyl-phenylsulfonium, and tribenzylsulfonium. Of these, preferred are triphenylsulfonium, 4-tert-butoxyphenyldiphenylsulfonium, dimethylphenylsulfonium, and 4-tert-butylphenyldiphenylsulfonium.

Especially useful onium salts are: diphenyliodonium 4-phenylmethylbenzenesulfonate, diphenyliodonium 4-(diphenylmethyl)benzenesulfonate, diphenyliodonium 4-(1'-methyl-1'-phenyl)ethylbenzenesulfonate, bis(4-tert-butylphenyl)iodonium 4-phenylmethylbenzenesulfonate, bis(4-tert-butylphenyl)iodonium 4-(diphenylmethyl)benzenesulfonate, bis(4-tert-butylphenyl)iodonium 4-(1'-methyl-1'-phenyl)ethylbenzenesulfonate, 4-methoxyphenylphenyliodonium 4-phenylmethylbenzenesulfonate, 4-methoxyphenylphenyliodonium 4-(diphenylmethyl)benzenesulfonate, 4-methoxyphenylphenyliodonium 4-(1'-methyl-1'-phenyl)ethylbenzenesulfonate, 4-tert-butoxyphenylphenyliodonium 4-phenylmethylbenzenesulfonate, 4-tert-butoxyphenylphenyliodonium 4-(diphenylmethyl)benzenesulfonate, 4-tert-butoxyphenylphenyliodonium 4-(1'-methyl-1'-phenyl)ethylbenzenesulfonate, triphenylsulfonium 4-phenylmethylbenzenesulfonate, triphenylsulfonium 4-(diphenylmethyl)benzenesulfonate, triphenylsulfonium 4-(1'-methyl-1'-phenyl)ethylbenzenesulfonate, 4-tert-butoxyphenyldiphenylsulfonium 4-phenylmethylbenzenesulfonate, 4-tert-butoxyphenyldiphenylsulfonium 4-(diphenylmethyl)benzenesulfonate, 4-tert-butoxyphenyldiphenylsulfonium 4-(1'-methyl-1'-phenyl)ethylbenzenesulfonate, 4-tert-butylphenyldiphenylsulfonium 4-phenylmethylbenzenesulfonate, 4-tert-butylphenyldiphenylsulfonium 4-(1'-methyl-1'-phenyl)ethylbenzenesulfonate, dimethylphenylsulfonium 4-phenylmethylbenzenesulfonate, and tris(4-tert-butoxyphenyl)sulfonium 4-(1'-methyl-1'-phenyl)ethylbenzenesulfonate.

The onium salts can be synthesized by the following method although the synthesis method is not limited thereto.

The substituted phenylmethylbenzenesulfonate anion of the onium salt according to the invention may be obtained by sulfonating a phenylmethane derivative in a conventional manner.

More particularly, reaction is effected with a sulfonating agent such as sulfuric acid, sulfur trioxide, chlorosulfonic acid, sulfur trioxide-pyridine complex or sulfur trioxide-dioxane complex as such or diluted with a solvent such as acetic anhydride, dichloromethane, acetic acid or ethyl acetate. With respect to the reaction conditions, reference should be made to New Experimental Chemistry Lecture, Vol. 14, Synthesis of Organic Compounds III, Maruzen K. K., 1986, pp. 1773–1784.

Specifically, a phenylmethane derivative is dissolved in a solvent such as dichloromethane. At room temperature or under cooling, chlorosulfonic acid is added to the solution. If the amount of chlorosulfonic acid is excessive relative to the phenylmethane derivative, two or more sulfonic acid moieties can be incorporated in a common molecule. Alternatively, a phenylmethane derivative is dissolved in a solvent such as acetic anhydride and sulfonated with sulfuric acid.

The process for the synthesis of corresponding sulfonium and iodonium salts is not critical although the preferred anions are halide ions and alkylsulfonic acids having a lower acid strength than arylsulfonic acids. It is noted that a sulfonium salt having a strong acid such as trifluoromethanesulfonic acid is difficult to effect anion exchange with the above-synthesized substituted phenylmethylbenzenesulfonic acid. When an onium salt having a strong acid anion is used as a starting reactant, it is desirable to first effect anion exchange using an ion-exchange chromatogram as described in JP-A 7-333844, obtaining an onium salt having a hydroxide ion, followed by further anion exchange with the above substituted phenylmethylbenzenesulfonic acid anion. The sulfonium and iodonium salts can be synthesized according to the teachings of The Chemistry of Sulfonium Group, Part 1, John-Wiley & Sons (1981), Advanced Photochemistry, vol. 17, John-Wiley & Sons (1992), J. Org. Chem., 1988, 53, 5571–5573, and JP-A 7-25846.

The anion exchange is desirably effected using at least 1 mol and more desirably 1 to 3 mol of the above-synthesized substituted phenylmethylbenzenesulfonic acid anion per mol of the onium salt, though the reaction conditions are not limited thereto. The solvent system may be an alcoholic solvent such as methanol or ethanol or a two layer system such as a dichloromethane/water mixture. For anion exchange of onium salts having a halide ion such as sulfonium chloride, the use of lead carbonate as described in JP-A 9-323970 ensures more quantitative exchange.

The onium salts of formulae (1), (1a), (1a') and (1b) find best use as the photoacid generator in resist materials, especially chemical amplification type resist materials although the application of the onium salts is not limited thereto. The invention provides resist compositions comprising onium salts of formulae (1), (1a), (1a') and (1b) as the photoacid generator.

Resist Composition

The onium salts of formulae (1), (1a), (1a') and (1b) are useful as the photoacid generator in chemical amplification type resist compositions. The resist compositions may be either positive or negative working.

The resist compositions of the invention include a variety of embodiments, 1) a chemically amplified positive working resist composition comprising (A) a resin which changes its solubility in an alkaline developer under the action of an acid, (B) an onium salt capable of generating an acid upon exposure to radiation of formula (1), (1a), (1a') or (1b), and (G) an organic solvent;

2) a chemically amplified positive working resist composition of 1) further comprising (C) a photoacid generator capable of generating an acid upon exposure to radiation other than component (B);

3) a chemically amplified positive working resist composition of 1) or 2) further comprising (D) a basic compound;

4) a chemically amplified positive working resist composition of 1) to 3) further comprising (E) an organic acid derivative;

5) a chemically amplified positive working resist composition of 1) to 4) further comprising (F) a compound with a molecular weight of up to 3,000 which changes its solubility in an alkaline developer under the action of an acid;

6) a chemically amplified negative working resist composition comprising (B) an onium salt capable of generating an acid upon exposure to radiation of formula (1), (1a), (1a') or (1b), (H) an alkali-soluble resin, (I) an acid crosslinking agent capable of forming a crosslinked structure under the action of an acid, and (G) an organic solvent;

7) a chemically amplified negative working resist composition of 6) further comprising (C) another photoacid generator;

8) a chemically amplified negative working resist composition of 6) or 7) further comprising (D) a basic compound; and 9) a chemically amplified negative working resist composition of 6), 7) or 8) further comprising (J) an alkali-soluble compound with a molecular weight of up to 2,500; but not limited thereto.

Moreover, the invention provides a process for forming a pattern, comprising the steps of applying the resist composition defined above onto a substrate (wafer) to form a coating; heat treating the coating and exposing the coating to high energy radiation with a wavelength of up to 300 nm or electron beam through a photo-mask; optionally heat treating the exposed coating, and developing the coating with a developer.

Now the respective components of the resist composition are described in detail.

Component (G)

Component (G) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylene sulfone. Of these, the propylene glycol alkyl ether acetates and alkyl lactates are especially preferred.

It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred. These solvents may be used alone or in admixture. An exemplary useful solvent mixture is a mixture of a propylene glycol alkyl ether acetate and an alkyl lactate. When the propylene glycol alkyl ether acetate is added as a solvent, it should preferably account for at least 50% by weight of the entire solvent. Similarly when the alkyl lactate is added as a solvent, it should preferably account for at least 50% by weight of the entire solvent. When a mixture of the propylene glycol alkyl ether acetate and the alkyl lactate is added as a solvent, it should preferably account for at least 50% by weight of the entire solvent. The mixing ratio of the propylene glycol alkyl ether acetate and the alkyl lactate is not critical although it is preferred to mix 50 to 99 parts by weight of the propylene glycol alkyl ether acetate with 50 to 1 parts by weight of the alkyl lactate. It is more preferred to mix 60 to 95% by weight of the propylene glycol alkyl ether acetate with 40 to 5% by weight of the alkyl lactate. A lower proportion of the propylene glycol alkyl ether acetate would invite a problem of inefficient coating whereas a higher proportion thereof would provide insufficient dissolution and allow for particle and defect (scum) formation. A lower proportion of the alkyl lactate would provide insufficient dissolution and cause the problem of many particles and defect (scum) whereas a higher proportion thereof would lead to a composition which has a too high viscosity to apply and loses storage stability. The solvent mixture of the propylene glycol alkyl ether acetate and the alkyl lactate may further contain one or more other solvents.

Component (A)

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups represented by C—O—C or C—O—Si linkages.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, methacrylic acid and acrylic acid, and such copolymers having a carboxylic derivative or diphenyl ethylene introduced at their terminus.

Also included are copolymers in which units free of alkali-soluble sites such as styrene, α-methylstyrene, acrylate, methacrylate, hydrogenated hydroxystyrene, maleic anhydride and maleimide are introduced in addition to the above-described units in such a proportion that the solubility in an alkaline developer may not be extremely reduced. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins are given below. These polymers may also be used as the material from which the resin (A) which changes its solubility in an alkaline developer under the action of an acid is prepared and as the alkali-soluble resin which serves as component (H) to be described later. Examples include poly(p-hydroxystyrene), poly(m-hydroxystyrene), poly(4-hydroxy-2-methylstyrene), poly(4-hydroxy-3-methylstyrene), poly(a-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methyl acrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxy-styrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers.

Alkali-soluble resins comprising units of the following formula (2) or (2') are especially preferred.

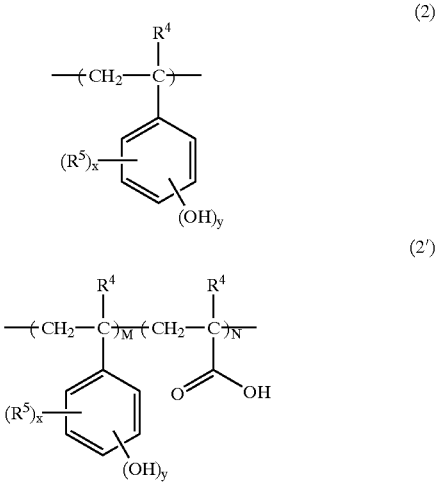

Herein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, and M and N are positive integers, satisfying $0<N/(M+N) \leq 0.5$.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of Up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

In the resist composition using an onium salt of formula (1), (1a), (1a') or (1b), a resin having such substituent groups with C—O—C or C—O—Si linkages (acid labile groups) that the solubility in an alkaline developer changes as a result of cleavage of the C—O—C or C—O—Si linkages under the action of an acid, especially an alkali-soluble resin as mentioned above is preferably used as component (A). Especially preferred is a polymer comprising recurring units of the above formula (2) and containing phenolic hydroxyl groups in which hydrogen atoms of the phenolic hydroxyl group are substituted by acid labile groups of one or more types in a proportion of more than 0 mol % to 80 mol % on the average of the entire hydrogen atoms of the phenolic hydroxyl group, the polymer having a weight average molecular weight of 3,000 to 100,000.

Also preferred is a polymer comprising recurring units of the above formula (2'), that is, a copolymer comprising p-hydroxystyrene and/or α-methyl-p-hydroxystyrene and acrylic acid and/or methacrylic acid, wherein some of the hydrogen atoms of carboxyl groups of the acrylic acid and/or methacrylic acid are replaced by acid labile groups of one or more types to form an ester, the units based on the acrylic ester and/or methacrylic ester are contained in a proportion of more than 0 molt to 50 mol %, on the average, of the copolymer, and wherein some of the hydrogen atoms of the phenolic hydroxyl groups of p-hydroxystyrene and/or α-methyl-p-hydroxystyrene may be substituted by acid labile groups of one or more types. Further preferred is such a copolymer in which the units based on the acrylic ester and/or methacrylic ester and the p-hydroxystyrene and/or α-methyl-p-hydroxystyrene having acid labile groups substituted thereon are contained in a proportion of more than 0 mol % to 80 mol %, on the average, of the copolymer.

Exemplary such polymers are polymers comprising recurring units represented by the following general formula 2a) or (2a') and having a weight average molecular weight of 3,000 to 100,000.

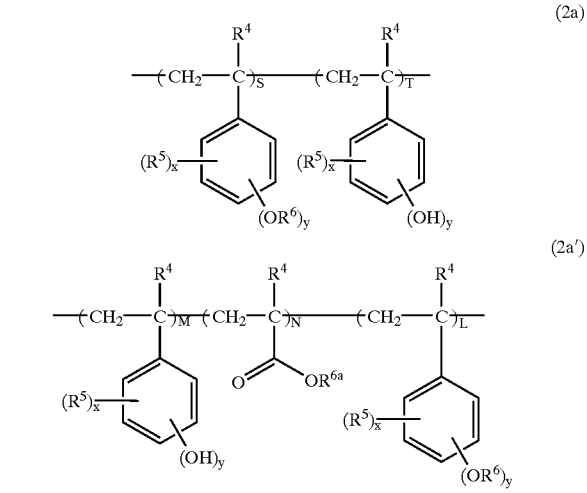

Herein, $R^4$ is hydrogen or methyl. $R^5$ is a straight, branched or cyclic alkyl group of 1 to 8 carbon atoms. $R^6$ is an acid labile group. $R^{6a}$ is hydrogen or an acid labile group, at least some, preferably all of the $R^{6a}$ groups are acid labile groups. Letter x is 0 or a positive integer, and y is a positive integer, satisfying $x+y \leq 5$. The $R^6$ groups may be the same or different when y is 2 or more. S and T are positive integers, satisfying $0<S/(S+T) \leq 0.8$. M and N are positive integers, L is 0 or a positive integer, satisfying $0<N/(M+N) \leq 0.5$ and $0<(N+L)/(M+N+L) \leq 0.8$.

$R^5$ stands for straight, branched or cyclic $C_{1-8}$ alkyl groups, for example, methyl, ethyl, propyl, isopropyl, n-butyl, isobutyl, tert-butyl, cyclohexyl and cyclopentyl.

With respect to the acid labile groups, where some of the phenolic hydroxyl groups and some or all of the carboxyl groups in the alkali-soluble resin are protected with acid labile groups having C—O—C linkages (or C—O—Si linkage), the acid labile groups are selected from a variety of such groups. The preferred acid labile groups are groups of the following general formulae (4) to (7), tertiary alkyl group of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

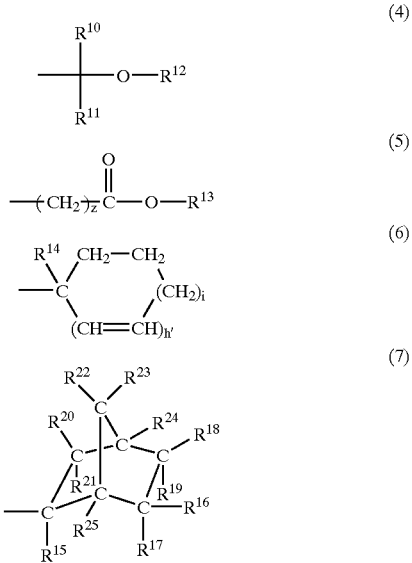

Herein $R^{10}$ and $R^{11}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{12}$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are replaced by hydroxyl, alkoxy, oxo, amino or alkylamino groups. Illustrative examples of the substituted alkyl groups are given below.

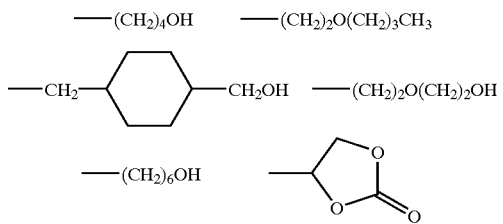

A pair of $R^{10}$ and $R^{11}$, a pair of $R^{10}$ and $R^{12}$, or a pair of $R^{11}$ and $R^{12}$, taken together, may form a ring. Each of $R^{10}$, $R^{11}$ and $R^{12}$ is a straight or branched alkylene group of 1 to 18 carbon atoms, preferably 1 to 10 carbon atoms, when they form a ring.

$R^{13}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (4). Exemplary tertiary alkyl groups are tert-butyl, tert-amyl, 1,1-diethylpropyl, 1-methylcyclopentyl, 1-ethylcyclopentyl, 1-isopropylcyclopentyl, 1-butylcyclopentyl, 1-methylcyclohexyl, 1-ethylcyclohexyl, 1-isopropylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxoran-4-yl. Letter z is an integer of 0 to 6.

$R^{14}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h' is equal to 0 or 1, i is equal to 0, 1, 2 or 3, satisfying 2h'+i=2 or 3.

$R^{15}$ is a straight, branched or cyclic alkyl group of 1 to 8 carbon atoms or substituted or unsubstituted aryl group of 6 to 20 carbon atoms, examples of which are as exemplified for $R^{14}$. $R^{16}$ to $R^{25}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, and sulfo groups. $R^{16}$ to $R^{25}$, for example, a pair of $R^{16}$ and $R^{17}$, a pair of $R^{16}$ and $R^{18}$, a pair of $R^{17}$ and $R^{19}$, a pair of $R^{18}$ and $R^{19}$, a pair of $R^{20}$ and $R^{21}$, or a pair of $R^{22}$ and $R^{23}$, taken together, may form a ring. When $R^{16}$ to $R^{25}$ form a ring, they are divalent $C_{1-15}$ hydrocarbon groups which may contain a hetero atom, examples of which are the above-exemplified monovalent hydrocarbon groups with one hydrogen atom eliminated. Also, two of $R^{16}$ to $R^{25}$ which are attached to adjacent carbon atoms (for example, a pair of $R^{16}$ and $R^{18}$, a pair of $R^{18}$ and $R^{24}$, or a pair of $R^{22}$ and $R^{24}$ may directly bond together to form a double bond.

Of the acid labile groups of formula (4), illustrative examples of the straight or branched groups are given below.

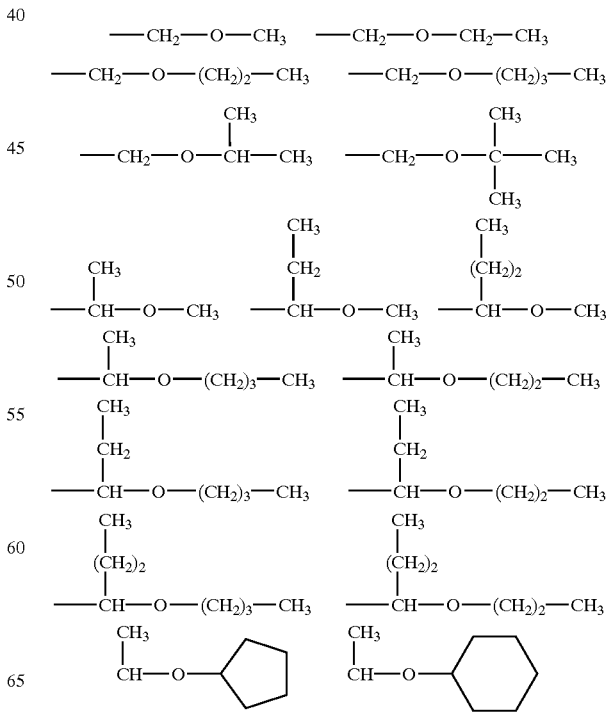

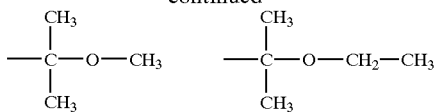

Of the acid labile groups of formula (4), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (5) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (6) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Illustrative examples of the acid labile groups of formula (7) are given below.

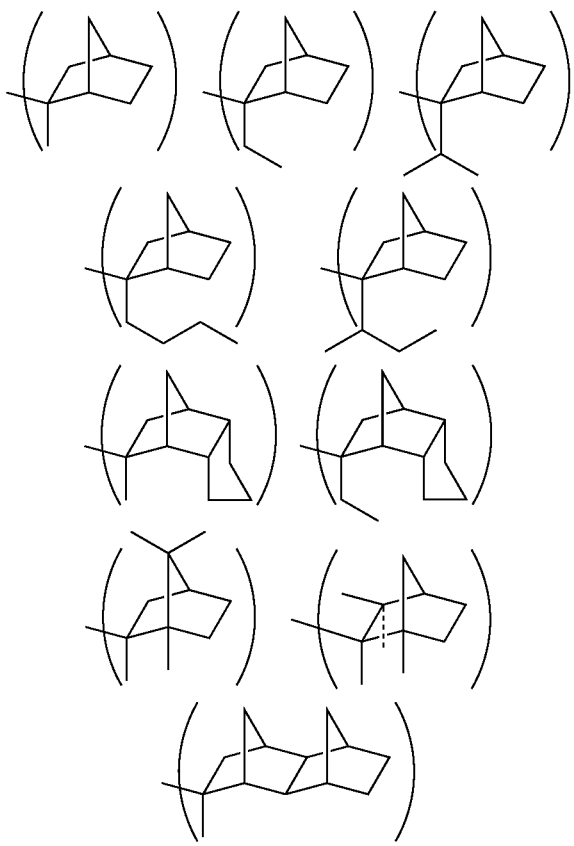

Exemplary of the tertiary alkyl group of 4 to 20 carbon atoms, preferably 4 to 15 carbon atoms, are tert-butyl, tert-amyl, 3-ethyl-3-pentyl and dimethylbenzyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

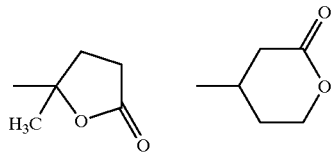

Exemplary of the aryl-substituted alkyl groups of 7 to 20 carbon atoms are benzyl, methylbenzyl, dimethylbenzyl, diphenylmethyl, and 1,1-diphenylethyl.

In the resist composition comprising an onium salt of formula (1), (1a), (1a') or (1b), the resin (A) may be the polymer of formula (2) or (2') in which some of the hydrogen atoms of the phenolic hydroxyl groups and/or all of the carboxyl groups are partially replaced by acid labile groups of one or more types, and the hydrogen atoms of the remaining phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3a) or (3b).

The crosslinking groups having C—O—C linkages are groups represented by the following general formula (3a) or (3b), preferably the following general formula (3a') or (3b').

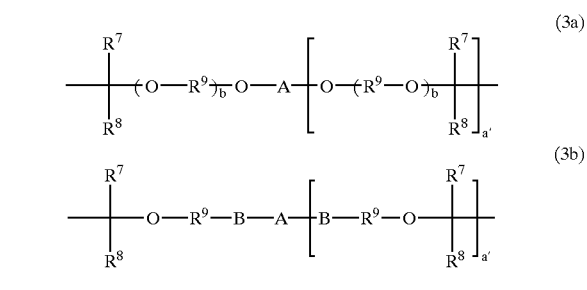

Herein, each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring. $R^9$ is a straight, branched or cyclic alkylene group of 1 to 10 carbon atoms, letter a' is an integer of 1 to 7, letter b is 0 or an integer of 1 to 10. A is an (a'+1)-valent aliphatic or alicyclic saturated hydrocarbon group, aromatic hydrocarbon group or heterocyclic group of 1 to 50 carbon atoms, which may be separated by a hetero atom and in which some of the hydrogen atoms attached to carbon atoms may be replaced by hydroxyl, carboxyl, carbonyl or halogen. B is —CO—O—, —NHCO—O— or —NHCONH—.

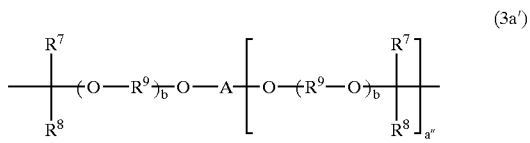

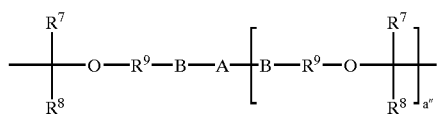
(3b′)

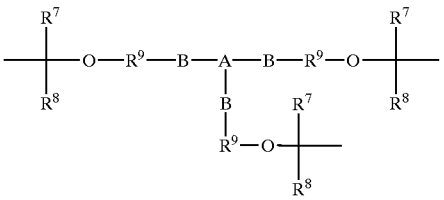
(3b‴)

Herein, each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring. $R^9$ is a straight, branched or cyclic alkylene group of 1 to 10 carbon atoms, letter a″ is an integer of 1 to 3, letter b is 0 or an integer of 1 to 5. A is an (a″+1)-valent straight, branched or cyclic alkylene, alkyltriyl or alkyltetrayl group of 1 to 20 carbon atoms or arylene group of 6 to 30 carbon atoms, which may be separated by a hetero atom and in which some of the hydrogen atoms attached to carbon atoms may be replaced by hydroxyl, carboxyl, acyl or halogen. B is —CO—O—, —NHCO—O— or —NHCONH—.

Examples of the straight, branched or cyclic $C_{1-8}$ alkyl group represented by $R^7$ and $R^8$ are as exemplified for $R^5$.

Examples of the straight, branched or cyclic $C_{1-10}$ alkylene group represented by $R^9$ include methylene, ethylene, propylene, isopropylene, n-butylene, isobutylene, cyclohexylene, and cyclopentylene.

Exemplary halogen atoms are fluorine, chlorine, bromine and iodine.

Illustrative examples of A are described later. These crosslinking groups of formulae (3a) and (3b) originate from alkenyl ether compounds and halogenated alkyl ether compounds to be described later.

As understood from the value of a′ in formula (3a) or (3b), the crosslinking group is not limited to a divalent one and trivalent to octavalent groups are acceptable. For example, the divalent crosslinking group is exemplified by groups of the following formulas (3a″) and (3b″), and the trivalent crosslinking group is exemplified by groups of the following formulas (3a‴) and (3b‴).

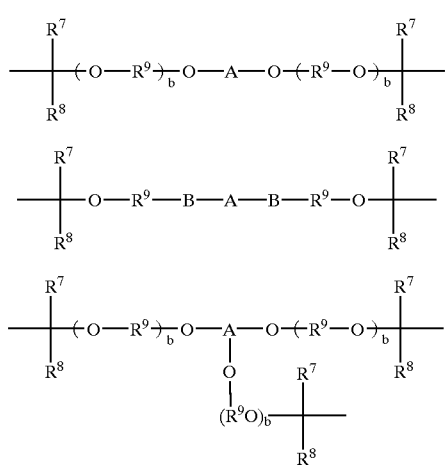

In the resist composition of the invention, the preferred polymer is a polymer comprising recurring units of the following general formula (2b) or (2b′), and more preferably the same polymer in which hydrogen atoms of phenolic hydroxyl groups represented by R are eliminated to leave oxygen atoms which are crosslinked within a molecule and/or between molecules with crosslinking groups having C—O—C linkages represented by the above formula (3a) or (3b).

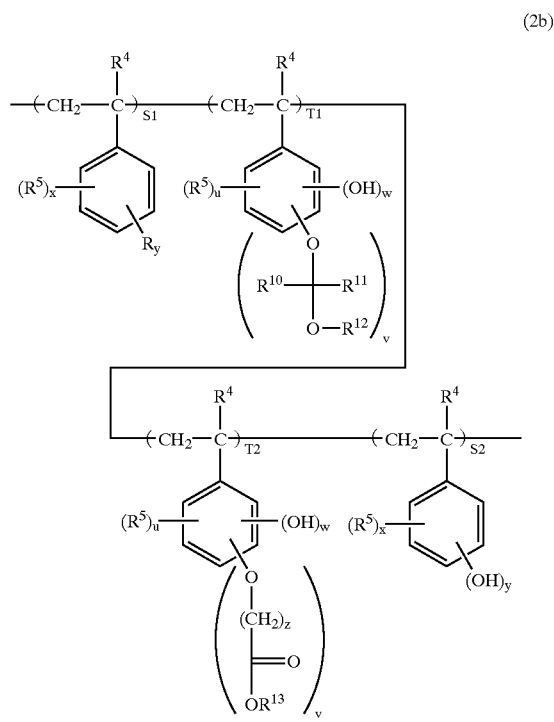
(2b)

Herein, R represents hydroxyl group or an acid labile group attached to an oxygen atom (i.e., —O— acid labile group) excluding —OCR$^{10}$R$^{11}$OR$^{12}$ and —O(CH$_2$)$_z$COOR$^{13}$. $R^4$ is hydrogen or methyl, $R^5$ is a straight, branched or cyclic alkyl group of 1 to 8 carbon atoms. $R^{10}$ and $R^{11}$ are independently hydrogen or straight, branched or cyclic alkyl groups of 1 to 18 carbon atoms, $R^{12}$ is a monovalent hydrocarbon group of 1 to 18 carbon atoms which may have a hetero atom, or $R^{10}$ and $R^{11}$, $R^{10}$ and $R^{12}$, or $R^{11}$ and $R^{12}$, taken together, may form a ring, with the proviso that each of $R^{10}$, $R^{11}$ and $R^{12}$ is a straight or branched alkylene group of 1 to 18 carbon atoms when they form a ring. $R^{13}$ is a tertiary alkyl group of 4 to 20 carbon atoms, an aryl-substituted alkyl group of 7 to 20 carbon atoms, an oxoalkyl group of 4 to 20 carbon atoms or a group represented by —CR$^{10}$R$^{11}$OR$^{12}$. Letter z is an integer of 0 to 6. S2 is a positive number, each of S1, T1, and T2 is 0 or a positive number, satisfying $0 \leq S1/(S1+T1+T2+S2) \leq 0.8$, $0 \leq T1/(S1+T1+T2+S2) \leq 0.8$, $0 \leq T2/(S1+T1+T2+S2) \leq 0.8$, and S1+T1+T2+S2=1. T1 and T2 are not equal to 0 at the same time. Each of u and w is 0 or a positive integer, and v is a positive integer, satisfying u+v+w≦5. Letters x and y are as defined above.

More preferably, S1, S2, T1 and T2 satisfy the following ranges.

$0 \leq S1/(S1+T1+T2+S2) \leq 0.5$,
especially $0.002 \leq S1/(S1+T1+T2+S2) \leq 0.2$
$0 \leq T1/(S1+T1+T2+S2) \leq 0.5$,
especially $0 \leq T1/(S1+T1+T2+S2) \leq 0.4$
$0 \leq T2/(S1+T1+T2+S2) \leq 0.5$,
especially $0 \leq T2/(S1+T1+T2+S2) \leq 0.4$
$0.4 \leq S2/(S1+T1+T2+S2) \leq 1$,
especially $0.5 \leq S2/(S1+T1+T2+S2) \leq 0.9$
$0 \leq (T1+T2)/(S1+T1+T2+S2) \leq 0.5$,
especially $0.1 \leq (T1+T2)/(S1+T1+T2+S2) \leq 0.4$ It is also preferred that T1/(T1+T2) be from 0 to 1, more preferably from 0.5 to 1, and most preferably from 0.7 to 1.

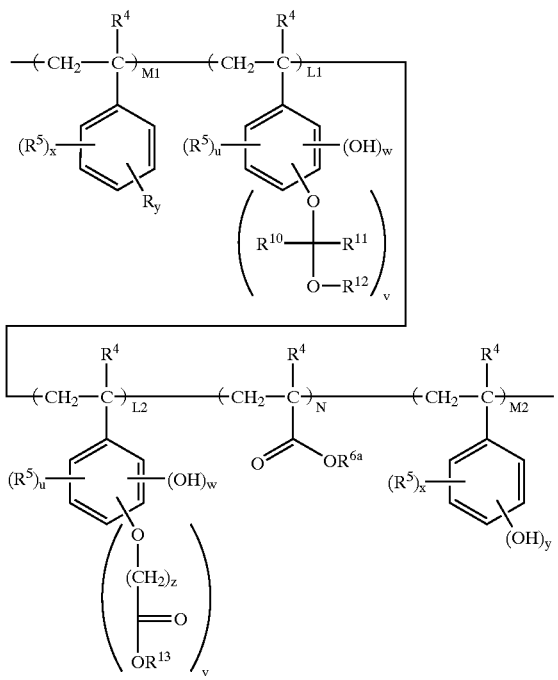

(2b')

Herein, R, $R^4$, $R^5$, $R^{10}$, $R^{11}$, $R^{12}$, $R^{13}$, x, y, z, u, v and w are as defined above. M2 is a positive number, each of M1, L1, L2 and N is 0 or a positive number, satisfying $0 \leq M1/(M1+L1+L2+N+M2) \leq 0.8$, $0 \leq L1/(M1+L1+L2+N+M2) \leq 0.8$, $0 \leq L2/(M1+L1+L2+N+M2) \leq 0.8$, $0 \leq N/(M1+L1+L2+N+M2) \leq 0.8$, and M1+L1+L2+N+M2=1. L1, L2 and N are not equal to 0 at the same time.

More preferably, M1, L1, L2, N and M2 satisfy the lo following ranges.

$0 \leq M1/(M1+L1+L2+N+M2) \leq 0.5$,
especially $0.002 \leq M1/(M1+L1+L2+N+M2) \leq 0.2$
$0 \leq L1/(M1+L1+L2+N+M2) \leq 0.5$,
especially $0 \leq L1/(M1+L1+L2+N+M2) \leq 0.4$
$0 \leq L2/(M1+L1+L2+N+M2) \leq 0.5$,
especially $0 < L2/(M1+L1+L2+N+M2) \leq 0.4$
$0 \leq N/(M1+L1+L2+N+M2) \leq 0.5$,
especially $0 \leq N/(M1+L1+L2+N+M2) \leq 0.4$
$0.4 \leq M2/(M1+L1+L2+N+M2) \leq 1$,
especially $0.5 \leq M2/(M1+L1+L2+N+M2) \leq 0.9$
$0 < (L1+L2+N)/(M1+L1+L2+N+M2) \leq 0.5$,
especially $0.1 \leq (L1+L2+N)/(M1+L1+L2+N+M2) \leq 0.4$ It is also preferred that N/(L1+L2+N) be from 0 to 1, more preferably from 0.5 to 1, and most preferably from 0.7 to 1.

In this polymer as well, the total amount of the acid labile groups including crosslinking groups is, on the average, more than 0 mol % to 80 mol % based on the entire phenolic hydroxyl groups in formula (2b) or the phenolic hydroxyl groups and carboxyl groups in formula (2b') combined.

Where the resin in the resist composition according to the invention is crosslinked with acid labile substituents, it is a polymer which is obtained by reacting phenolic hydroxyl groups with an alkenyl ether compound or halogenated alkyl ether such that the polymer is crosslinked within a molecular and/or between molecules with crosslinking groups having C—O—C linkages, wherein the total amount of the acid labile groups and crosslinking groups is preferably, on the average, more than 0 mol % to 80 mol %, especially 2 to 50 mol %, based on the entire phenolic hydroxyl groups in formula (2) or the phenolic hydroxyl groups and carboxyl groups in formula (2') combined.

An appropriate proportion of crosslinking groups having C—O—C linkages is, on the average, from more than 0 mol % to 50 mol %, and especially from 0.2 to 20 mol %. With 0 mol %, few benefits of the crosslinking group are obtained, resulting in a reduced contrast of alkali dissolution rate and a low resolution. With more than 50 mol %, a too much crosslinked polymer would gel, become insoluble in alkali, induce a film thickness change, internal stresses or bubbles upon alkali development, and lose adhesion to the substrate due to less hydrophilic groups.

The proportion of acid labile groups is on the average preferably from more than 0 mol % to 80 mol %, especially from 10 to 50 mol %. With 0 mol %, there may result a reduced contrast of alkali dissolution rate and low resolution. With more than 80 mol %, there may result a loss of alkali dissolution, less affinity to an alkali developer upon development, and a low resolution.

By properly selecting the proportions of crosslinking groups having C—O—C linkages and acid labile groups within the above-defined ranges, it becomes possible to control the size and configuration of a resist pattern as desired. In the resist composition comprising the onium salt according to the invention, the contents of crosslinking groups having C—O—C linkages and acid labile groups in the polymer have substantial influence on the dissolution rate contrast of a resist film and govern the properties of the resist composition relating to the size and configuration of a resist pattern.

Now A in the crosslinking group is described. The (a'+1)-valent organic groups represented by A include hydrocarbon groups, for example, substituted or unsubstituted alkylene groups preferably having 1 to 50 carbon atoms, and especially 1 to 40 carbon atoms, substituted or unsubstituted arylene groups preferably having 6 to 50 carbon atoms, and especially 6 to 40 carbon atoms (these alkylene and arylene groups may have an intervening hetero atom or group such as O, NH, N(CH$_3$), S or SO$_2$, and where substituted, the substituents are hydroxyl, carboxyl, acyl and fluorine), and combinations of these alkylene groups with these arylene groups, as well as a"-valent groups of the foregoing groups from which a hydrogen atom attached to a carbon atom is eliminated wherein a" is an integer of 3 to 8. Additional examples include (a'+1)-valent heterocyclic groups, and combinations of these heterocyclic groups with the foregoing hydrocarbon groups.

Illustrative examples of A are given below, although ethylene group, 1,2-propylene group, 1,3-propylene group, 1,3-butylene group, 1,4-butylene group, 2,2-dimethyl-1,3-propylene group and 1,4-cyclohexylene group are especially exemplified as A.
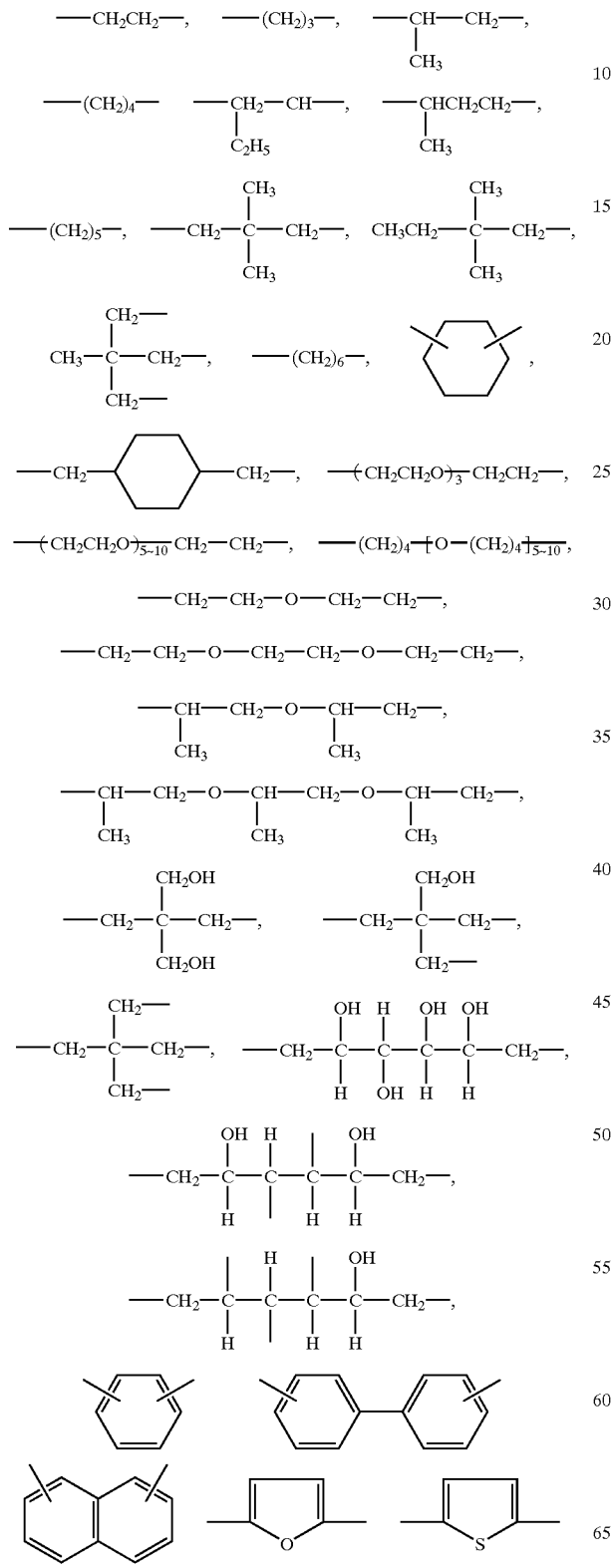
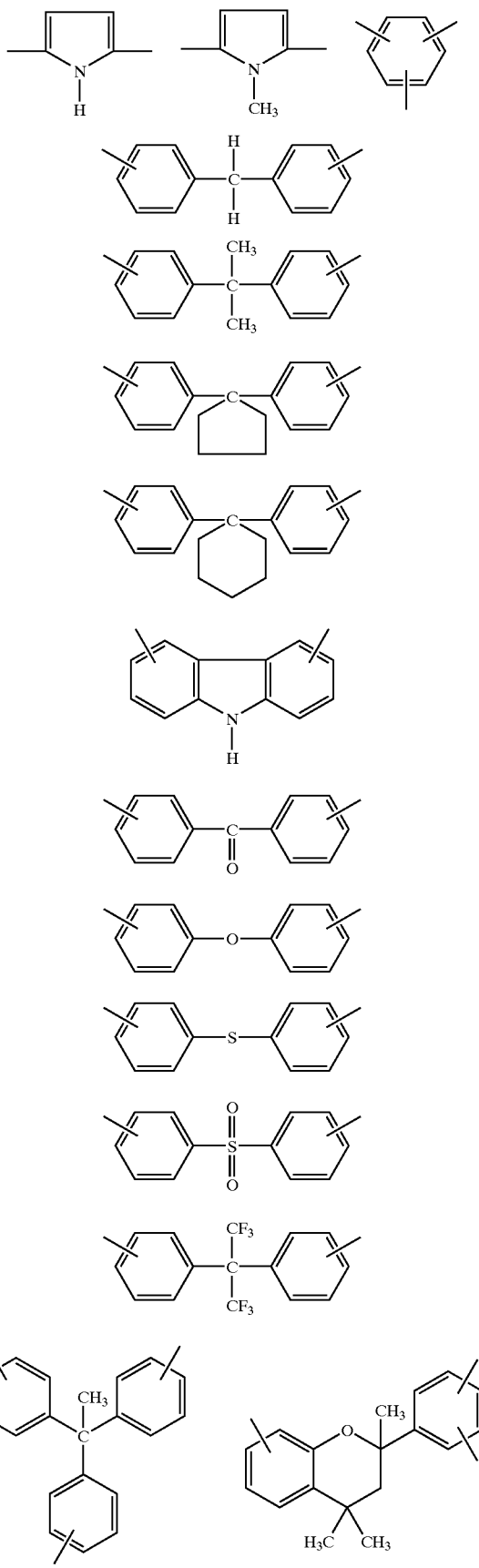

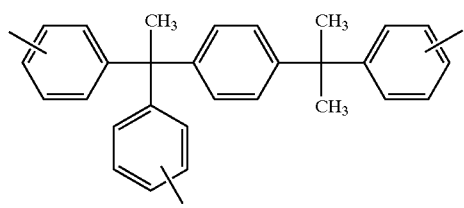

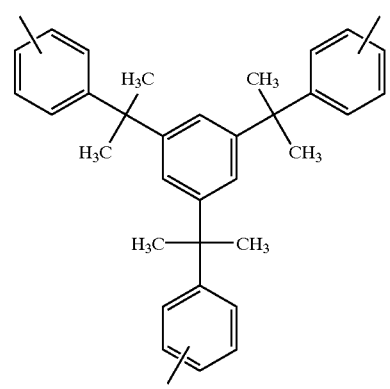

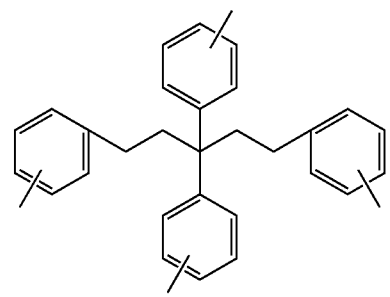

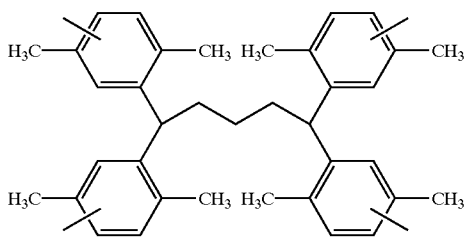

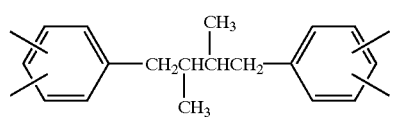

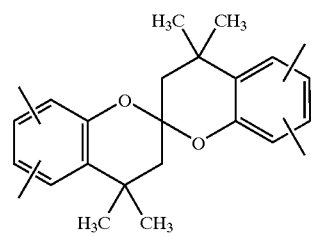

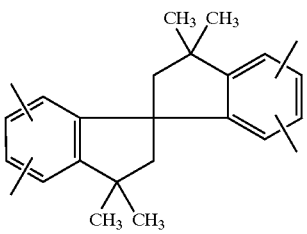

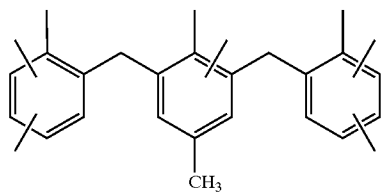

Preferably, in formula (3a), $R^7$ is methyl, $R^8$ is hydrogen, a' is equal to 1, b is equal to 0, and A is ethylene, 1,4-butylene or 1,4-cyclohexylene.

In preparing the polymer which is crosslinked within a molecular and/or between molecules with crosslinking groups having C—O—C linkages, synthesis may be made by reacting a corresponding non-crosslinked polymer with an alkenyl ether in the presence of an acid catalyst in a conventional manner.

Alternatively, where decomposition of other acid labile groups takes place in the presence of an acid catalyst, the end product can be synthesized by first reacting an alkenyl ether with hydrochloric acid or the like to form a halogenated alkyl ether, and reacting it with a polymer under basic conditions in a conventional manner.

The alkenyl ether may be one selected from ethyleneglycol divinyl ether, 1,2-propanediol divinyl ether, 1,4-butanediol divinyl ether and 1,4-cyclohexanediol divinyl ether, although not limited thereto.

More illustratively, non-limiting, examples of the alkenyl ether include ethylene glycol divinyl ether, triethylene glycol divinyl ether, 1,2-propanediol divinyl ether, 1,3-propanediol divinyl ether, 1,3-butanediol divinyl ether, 1,4-butanediol divinyl ether, tetramethylene glycol divinyl ether, neopentyl glycol divinyl ether, trimethylolpropane trivinyl ether, trimethylolethane trivinyl ether, hexanediol divinyl ether, 1,4-cyclohexanediol divinyl ether, 1,4-divinyloxymethylcyclohexane, tetraethylene glycol divinyl ether, pentaerythritol divinyl ether, pentaerythritol trivinyl ether, pentaerythritol tetravinyl ether, sorbitol tetravinyl ether, sorbitol pentavinyl ether, ethylene glycol diethylene vinyl ether, triethylene glycol diethylene vinyl ether, ethylene glycol dipropylene vinyl ether, triethylene glycol diethylene vinyl ether, trimethylolpropane triethylene vinyl ether, trimethylolpropane diethylene vinyl ether, pentaerythritol diethylene vinyl ether, pantaerythritol triethylene vinyl ether, pentaerythritol tetraethylene vinyl ether, and the compounds of the following formulae (I-1) through (I-31).

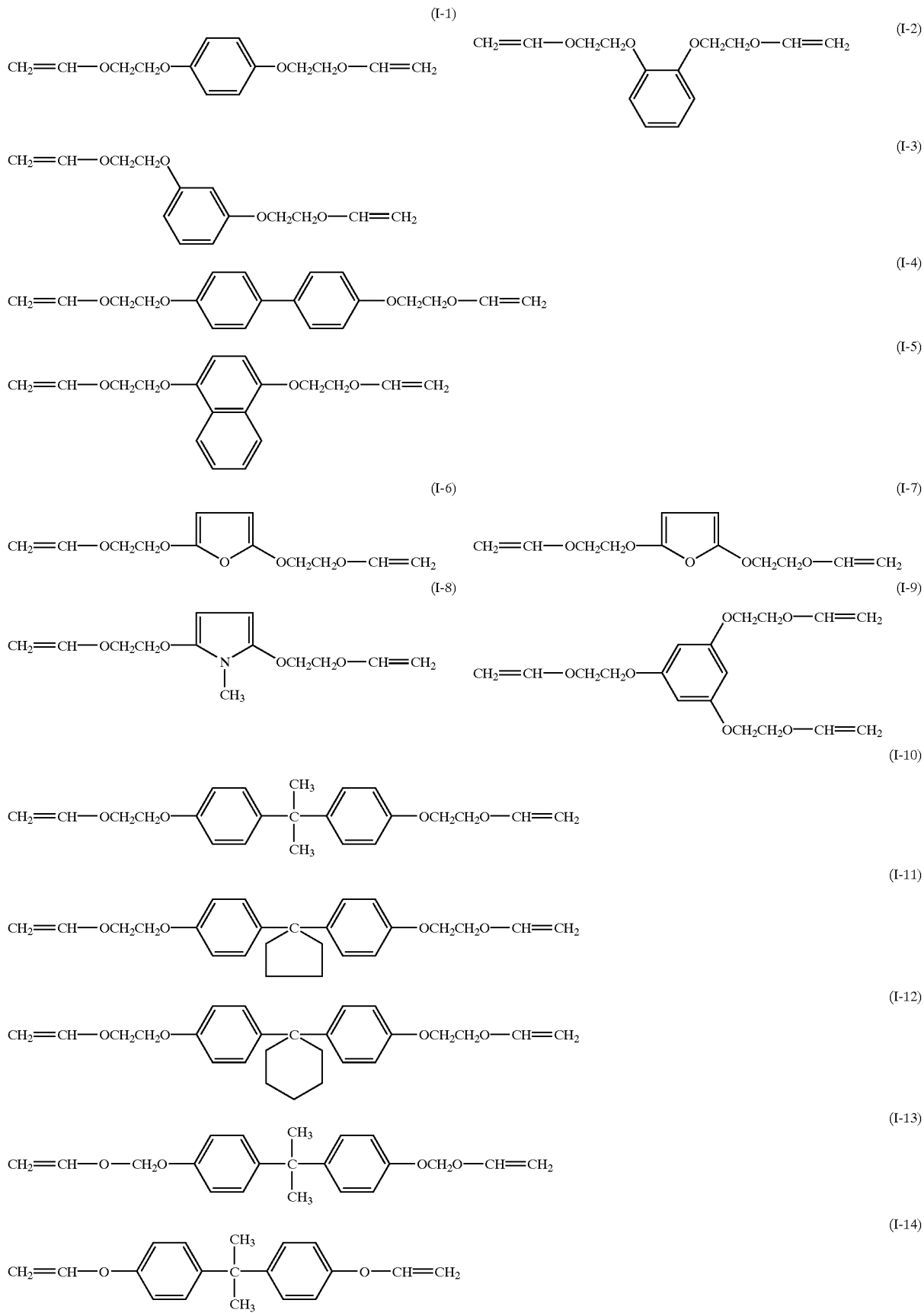

-continued
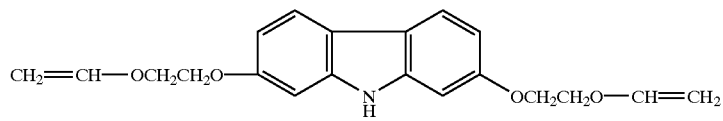 (I-15)
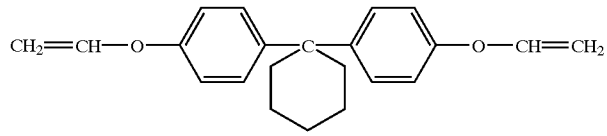 (I-16)
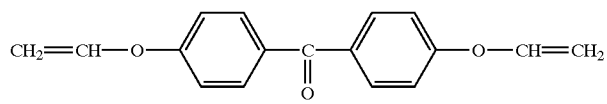 (I-17)
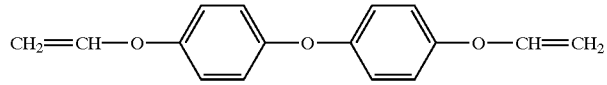 (I-18)
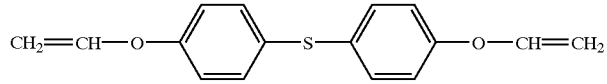 (I-19)
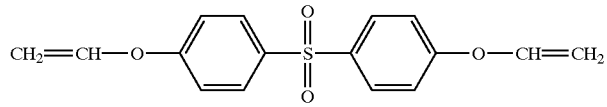 (I-20)
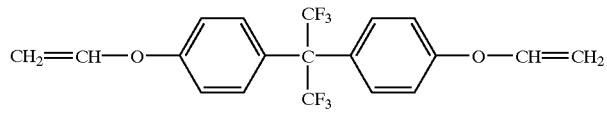 (I-21)
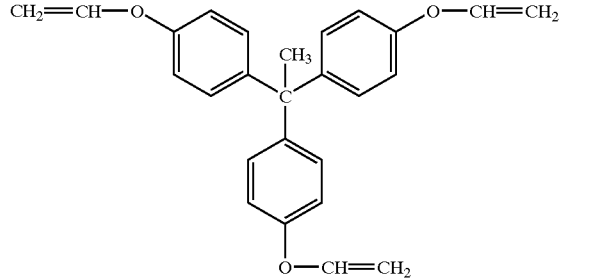 (I-22)
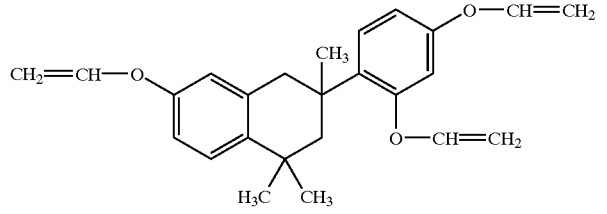 (I-23)
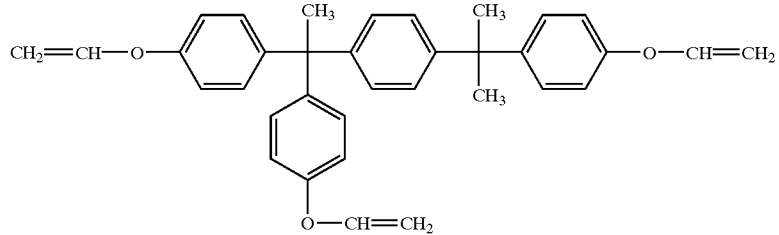 (I-24)

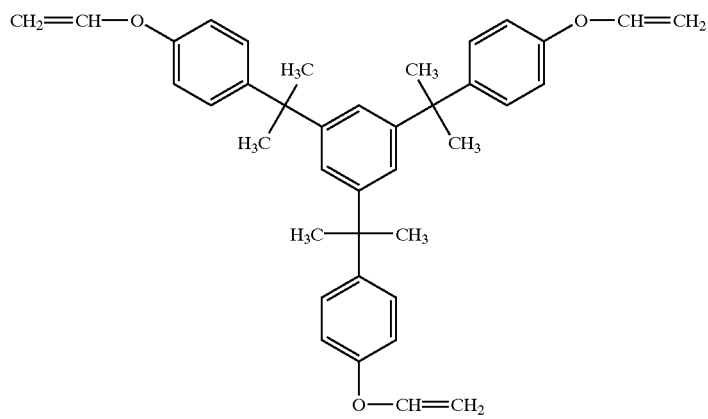
(I-25)
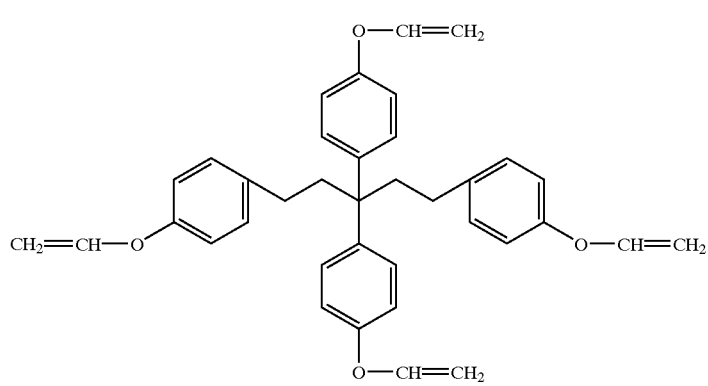
(I-26)
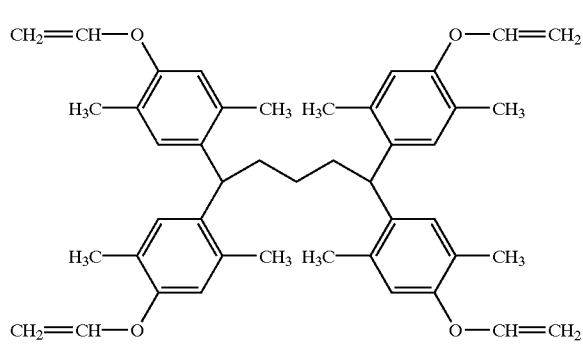
(I-27)
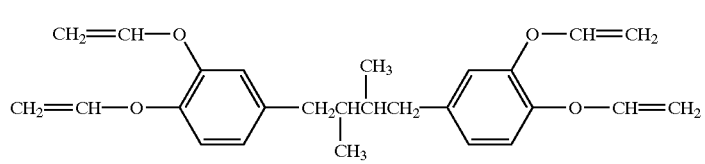
(I-28)
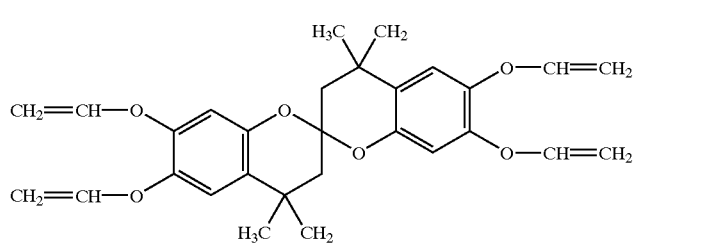
(I-29)

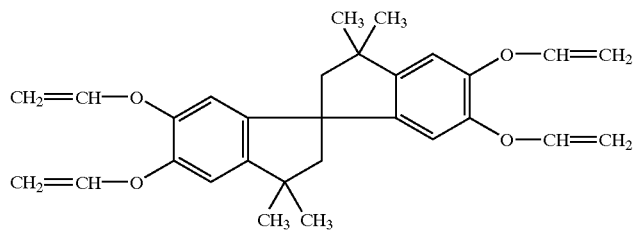

(I-30)

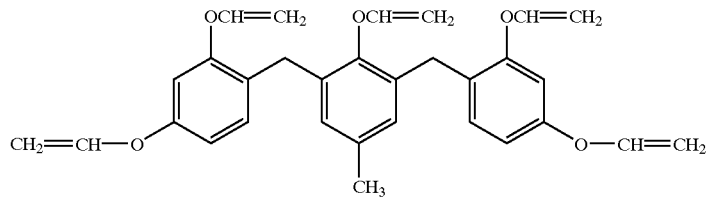

(I-31)

Also useful are terephthalic acid diethylene vinyl ether, phthalic acid diethylene vinyl ether, isophthalic acid diethylene vinyl ether, phthalic acid dipropylene vinyl ether, terephthalic acid dipropylene vinyl ether, isophthalic acid dipropylene vinyl ether, maleic acid diethylene vinyl ether, fumaric acid diethylene vinyl ether, itaconic acid diethylene vinyl ether as well as the compounds of the following formulae (II-1) through (II-11). Useful alkenyl ethers are not limited to these examples.

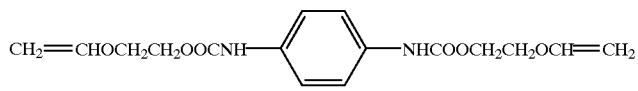

(II-1)

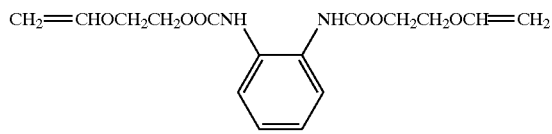

(II-2)

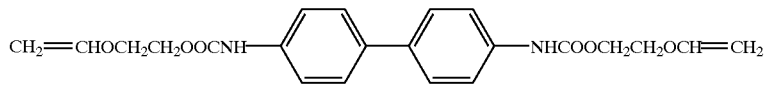

(II-3)

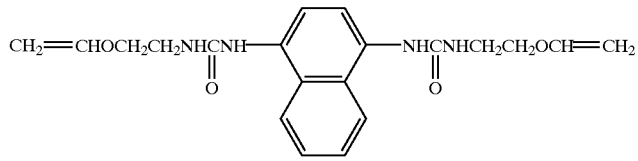

(II-4)

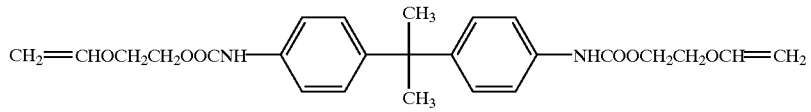

(II-5)

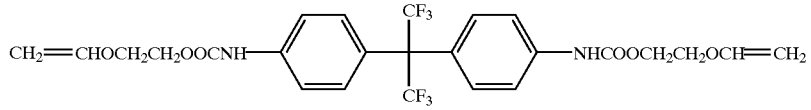

(II-6)

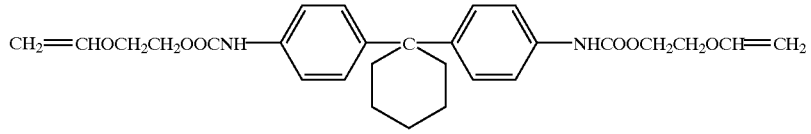

(II-7)

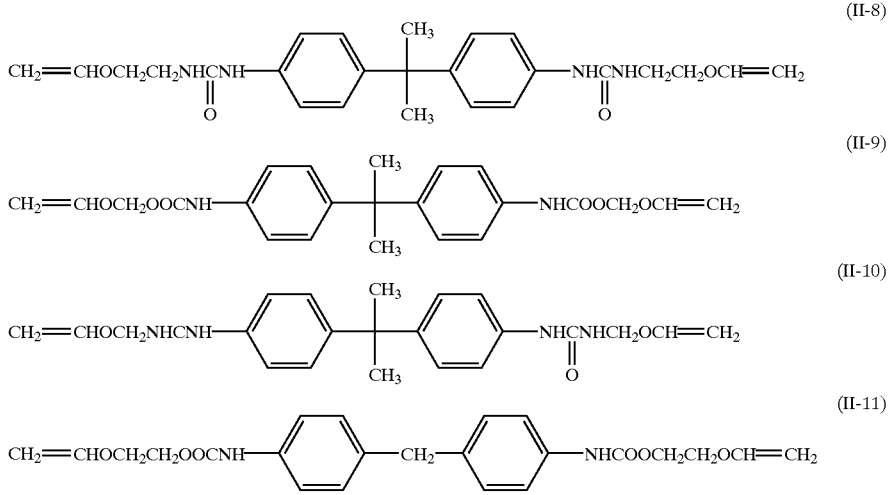

In the resist composition according to the invention, the resin used as component (A) is as described above while the preferred acid labile groups introduced therein are 1-ethylcyclohexyl, 1-ethylcyclopentyl, 1-ethylcyclohexyloxycarbonylmethyl, tert-amyl, 1-ethoxyethyl, 1-ethoxypropyl, tetrahydrofuranyl, tetrahydropyranyl, tert-butyl, tert-butoxycarbonyl, tert-butoxycarbonylmethyl groups, and substituents of formula (3a) wherein $R^7$ is methyl, $R^8$ is hydrogen, a' is 1, b is equal to 0, and A is ethylene, 1,4-butylene or 1,4-cyclohexylene.

In a single polymer, these substituents may be incorporated alone or in admixture of two or more types. A blend of two or more polymers having substituents of different types is also acceptable.

Appropriate combinations of substituents of two or more types include a combination of acetal with acetal analog, a combination of acetal with a substituent having a different degree of cleavage by acid such as tert-butoxy, a combination of a crosslinking acid labile group with acetal, and a combination of a crosslinking acid labile group with a substituent having a different degree of cleavage by acid such as tert-butoxy.

The percent proportion of these substituents substituting for phenol and carboxyl groups in the polymer is not critical. Preferably the percent substitution is selected such that when a resist composition comprising the polymer is applied onto a substrate (wafer) to form a coating, the unexposed area of the coating may have a dissolution rate of 0.01 to 10 Å/sec in a 2.38% tetramethylammonium hydroxide (TMAH) developer.

On use of a polymer containing a greater proportion of carboxyl groups which can reduce the alkali dissolution rate, the percent substitution must be increased or non-acid-labile substituents to be described later must be introduced.

When acid labile groups for intramolecular and/or intermolecular crosslinking are to be introduced, the percent proportion of crosslinking substituents is preferably up to 20 mol %, more preferably up to 10 mol %. If the percent substitution of crosslinking substituents is too high, crosslinking results in a higher molecular weight which can adversely affect dissolution, stability and resolution. It is also preferred to further introduce another non-crosslinking acid labile group into the crosslinked polymer at a percent substitution of up to 10 mol % for adjusting the dissolution rate to fall within the above range.

In the case of poly(p-hydroxystyrene), the optimum percent substitution differs between a substituent having a strong dissolution inhibitory action such as a tert-butoxycarbonyl group and a substituent having a weak dissolution inhibitory action such as an acetal group although the overall percent substitution is preferably 10 to 40 mol %, more preferably 20 to 30 mol %.

Polymers having such acid labile groups introduced therein should preferably have a weight average molecular weight (Mw) of 3,000 to 100,000. With a Mw of less than 3,000, polymers would perform poorly and often lack heat resistance and film formability. Polymers with a Mw of more than 100,000 would be less soluble in a developer and a resist solvent.

Where non-crosslinking acid labile groups are introduced, the polymer should preferably have a dispersity (Mw/Mn) of up to 3.5, preferably up to 1.5. A polymer with a dispersity of more than 3.5 often results in a low resolution. Where crosslinking acid labile groups are introduced, the starting alkali-soluble resin should preferably have a dispersity (Mw/Mn) of up to 1.5, and the dispersity is kept at 3 or lower even after protection with crosslinking acid labile groups. If the dispersity is higher than 3, dissolution, coating, storage stability and/or resolution is often poor.

To impart a certain function, suitable substituent groups may be introduced into some of the phenolic hydroxyl and carboxyl groups on the acid labile group-protected polymer. Exemplary are substituent groups for improving adhesion to the substrate, non-acid-labile groups for adjusting dissolution in an alkali developer, and substituent groups for improving etching resistance.

Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxoranyl, 4-methyl-2-oxo-4-oxanyl, methyl, ethyl, propyl, n-butyl, sec-butyl, acetyl, pivaloyl, adamantyl, isobornyl, and cyclohexyl.

Illustrative examples of the onium salts of formulae (1), (1a), (1a') and (1b) as the photoacid generator (B) are as described above.

Especially useful onium salts are: diphenyliodonium 4-phenylmethylbenzenesulfonate, diphenyliodonium 4-(diphenylmethyl)benzenesulfonate, diphenyliodonium 4-(1'-methyl-1'-phenyl)ethylbenzenesulfonate, bis(4-tertbutylphenyl)iodonium 4-phenylmethylbenzenesulfonate, bis(4-tert-butylphenyl)iodonium 4-(diphenylmethyl) benzenesulfonate, bis(4-tert-butylphenyl)iodonium 4-(1'-methyl-1'-phenyl)ethylbenzenesulfonate, 4-methoxyphenylphenyliodonium 4-phenylmethylbenzenesulfonate, 4-methoxyphenylphenyliodonium 4-(diphenylmethyl) benzenesulfonate, 4-methoxyphenylphenyliodonium 4-(1'-methyl-1'-phenyl)ethylbenzenesulfonate, 4-tert-butoxyphenylphenyliodonium 4-phenylmethylbenzenesulfonate, 4-tert-butoxyphenylphenyliodonium 4-(diphenylmethyl) benzenesulfonate, 4-tert-butoxyphenylphenyliodonium 4-(1'-methyl-1'-phenyl)ethylbenzenesulfonate, triphenylsulfonium 4-phenylmethylbenzenesulfonate, triphenylsulfonium 4-(diphenylmethyl)benzenesulfonate, triphenylsulfonium 4-(1'-methyl-di-phenyl)ethylbenzenesulfonate, 4-tert-butoxyphenyldiphenylsulfonium 4-phenylmethylbenzenesulfonate, 4-tert-butoxyphenyldiphenylsulfonium 4-(diphenylmethyl) benzenesulfonate, 4-tert-butoxyphenyldiphenylsulfonium 4-(1-methyl-1'-phenyl)ethylbenzenesulfonate, 4-tert-butylphenyldiphenylsulfonium 4-phenylmethylbenzenesulfonate, 4-tert-butylphenyldiphenylsulfonium 4-(1'-methyl-1'-phenyl) ethylbenzenesulfonate, dimethylphenylsulfonium 4-phenylmethylbenzenesulfonate, and tris(4-tert-butoxyphenyl)sulfonium 4-(1'-methyl-1'-phenyl) ethylbenzenesulfonate.

In the chemical amplification type resist composition, an appropriate amount of the onium salt (B) of formula (1), (1a), (1a') or (1b) added is from 0.5 part to 20 parts by weight, and preferably from 1 to 10 parts by weight, per 100 parts by weight of the solids in the composition. The photoacid generators may be used alone or in admixture of two or more. The transmittance of the resist film can be controlled by using a photoacid generator having a low transmittance at the exposure wavelength and adjusting the amount of the photoacid generator added.

Component (C)

In one preferred embodiment, the resist composition further contains (C) a compound capable of generating an acid upon exposure to high energy radiation, that is, a second photoacid generator other than the onium salt (B). Examples of the second photoacid generator include sulfonium salts, iodonium salts, sulfoniumdiazomethane compounds, N-sulfonyloxyimide photoacid generators, benzoinsulfonate photoacid generators, nitrobenzyl sulfonate photoacid generators, sulfone photoacid generators and glyoxime derivative photoacid generators are given below while they may be used alone or in admixture of two or more.

Sulfonium salts are salts of sulfonium cations with sulfonates. Exemplary sulfonium cations include triphenylsulfonium, (4-tert-butoxyphenyl) diphenylsulfonium, bis(4-tert-butoxyphenyl) phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl) sulfonium, (3,4-di-tert-butoxy-phenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxy-carbonylmethyloxyphenyl)diphenylsulfonium, tris(4-tert-butoxycarbonylmethyloxyphenyl)sulfonium, (4-tert-butoxy-phenyl)bis(4-dimethylaminophenyl)sulfonium, tris (4-dimethyl-aminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, diphenylmethylsulfonium, methyl-2-oxopropylphenylsulfonium, 2-oxocyclohexylcyclohexylmethylsulfonium, trinaphthylsulfonium, and tribenzylsulfonium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Sulfonium salts based on combination of the foregoing examples are included.

Iodonium salts are salts of iodonium cations with sulfonates. Exemplary iodonium cations are aryliodonium cations including diphenyliodonium, bis(4-tert-butylphenyl) iodonium, 4-tert-butoxyphenylphenyliodonium, and 4-methoxyphenylphenyliodonium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Iodonium salts based on combination of the foregoing examples are included.

Exemplary sulfonyldiazomethane compounds include bissulfonyldiazomethane compounds and sulfonyl-carbonyl-diazomethane compounds such as bis (ethylsulfonyl)diazomethane, bis(1-methylpropylsulfonyl) diazomethane, bis(2-methylpropylsulfonyl)diazomethane, bis(1,1-dimethylethylsulfonyl)diazomethane, bis (cyclohexylsulfonyl)diazomethane, bis (perfluoroisopropylsulfonyl)diazomethane, bis (phenylsulfonyl)diazomethane, bis(4-methylphenylsulfonyl)diazomethane, bis(2,4-dimethylphenylsulfonyl)diazomethane, bis(2-naphthylsulfonyl) diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo [2.2.1]-5-heptene-2,3-dicarboxylic acid imide. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, hydroquinone, in which all the hydroxyl groups are replaced by trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Also useful are analogous nitrobenzyl sulfonate compounds in which the nitro group on the benzyl side is replaced by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluene-sulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives include bis-o-(p-toluenesulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-o-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexylsulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, and bis-o-(camphorsulfonyl)-α-dimethylglyoxime.

Of these photoacid generators, the sulfonium salts, bis-sulfonyldiazomethane compounds, and N-sulfonyloxyimide compounds are preferred. While the anion of the optimum acid to be generated differs depending on the ease of scission of acid labile groups introduced in the polymer, an anion which is non-volatile and not extremely diffusive is generally chosen. The preferred anions include benzenesulfonic acid anions, toluenesulfonic acid anions, pentafluorobenzenesulfonic acid anions, 2,2,2-trifluoroethanesulfonic acid anions, nonafluorobutanesulfonic acid anions, heptadecafluorooctanesulfonic acid anions, and camphorsulfonic acid anions. The sulfonium salts and iodonium salts having such an anion are preferably used.

In the resist composition comprising the onium salt as the first photoacid generator according to the invention, an appropriate amount of the second photoacid generator (C) is 0 to 20 parts, and especially 1 to 10 parts by weight per 100 parts by weight of the solids in the composition. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition according to the invention, there may be added a compound which is decomposed with an acid to generate an acid, that is, acid-propagating compound. For these compounds, reference should be made to J. Photopolym. Sci. and Tech., 8, 43–44, 45–46 (1995), and ibid., 9, 29–30 (1996).

Examples of the acid-propagating compound include tert-butyl-2-methyl-2-tosyloxymethyl acetoacetate and 2-phenyl-2-(tosyloxyethyl)-1,3-dioxoran, but are not limited thereto. Of well-known photoacid generators, many of those compounds having poor stability, especially poor thermal stability exhibit an acid-propagating compound-like behavior.

In the resist composition according to the invention, an appropriate amount of the acid-propagating compound is up to 2 parts, and especially up to 1 part by weight per 100 parts by weight of the solids in the composition. Excessive amounts of the acid-propagating compound makes diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline lo derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]-piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

Also useful are substituted ones of the hydroxyl group-bearing nitrogenous compounds in which some or all of the hydrogen atoms of hydroxyl groups are replaced by methyl, ethyl, methoxymethyl, methoxyethoxymethyl, acetyl, or ethoxyethyl groups. Preferred are methyl-, acetyl-, methoxymethyl- and methoxyethoxymethyl-substituted compounds of ethanolamine, diethanolamine and triethanolamine. Examples include tris(2-methoxyethyl)amine, tris(2-ethoxyethyl)amine, tris(2-acetoxyethyl)amine, tris{2-(methoxymethoxy)ethyl}amine, tris{2-(methoxyethoxy)-ethyl}amine, tris[2-{(2-methoxyethoxy}methoxy)ethyl]amine, tris{2-(2-methoxyethoxy)ethyl}amine, tris{2-(1-methoxyethoxy)ethyl}amine, tris{2-(1-ethoxyethoxy)ethyl}amine, tris{2-(1-ethoxypropoxy)-ethyl}amine, and tris[2-{(2-hydroxyethoxy)ethoxy}ethyl]amine.

The basic compounds preferably used include triethylamine, tri-n-propylamine, triisopropylamine, tri-n-butylamine, triisobutylamine, tri-sec-butylamine, tripentylamine, phenethylamine, pyridine, aminopyridine, pyridinium p-toluene-solfonate, monoethanolamine, diethanolamine, triethanolamine, N-ethyldiethanolamine, N,N-diethylethanolamine, truisopropanolamine, 2,2'-iminodiethanol, 2-aminoethanol, 3-amino-1-propanol, 4-amino-1-butanol, 4-(2-hydroxyethyl)morpholine, N,N-dimethylacetamide, tris(2-methoxyethyl)amine, tris(2-ethoxyethyl)amine and tris{2-(methoxymethoxy)ethyl}amine.

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E) Illustrative, non-limiting, examples of the organic acid derivatives (E) include phenol, cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4'-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition according to the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

In one preferred embodiment, the resist composition further contains (F) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl) valeric acid, tris(4-hydroxyphenyl)methane, 1,1,1-tris(4'-hydroxyphenyl)ethane, 1,1,2-tris(4'-hydroxyphenyl)ethane, phenolphthalein, and thimolphthalein. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4'-tert-butoxycarbonylmethyloxyphenyl)propane, 2,2-bis(4'-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)valerate, tert-butyl 4,4-bis(4'-(2"-tetrahydrofuranyloxy)phenyl)valerate, tert-butyl 4,4-bis(4'-tert-butoxyphenyl)valerate, tert-butyl 4,4-bis(4'-tert-butoxycarbonyloxyphenyl)valerate, tert-butyl 4,4-bis(4'-tert-butoxycarbonylmethyloxyphenyl)valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2"-tetrahydropyranyloxy)phenyl)ethane, 1,1,2-tris(4'-(2"-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, and 1,1,2-tris(4'-(1'-ethoxypropyloxy)phenyl)ethane.

The dissolution inhibitors preferably used include 20 2,2-bis(4'-(2'-tetrahydropyranyloxy))propane, 2,2-bis(4'-tert-butoxycarbonyloxyphenyl)propane, tert-butyl 4,4-bis (4'-(2"-tetrahydropyranyloxy)phenyl)-valerate, tert-butyl 4,4-bis(4'-tert-butoxycarbonyloxyphenyl)valerate and tert-butyl 4,4-bis(4'-tert-butoxycarbonylmethyloxyphenyl)-valerate.

In the resist composition according to the invention, an appropriate amount of the dissolution inhibitor (F) is up to 20 parts, and especially up to 15 parts by weight per 100 parts by weight of the solids in the composition. With more than 20 parts of the dissolution inhibitor, the resist composition becomes less heat resistant because of an increased content of monomer components.

In a chemical amplification, negative working, resist composition as well, the onium salt of formula (1), (1a), (1a') or (1b) according to the invention may be used as the photoacid generator. This composition further contains an alkali-soluble resin as component (H), examples of which are intermediates of the above-described component (A) though not limited thereto. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly (acrylic acid), acrylic acid-methyl acrylate copolymers, methacrylic acid-methyl methacrylate copolymers, acrylic acid-maleimide copolymers, methacrylic acid-maleimide copolymers, p-hydroxystyreneacrylic acid-maleimide copolymers, and p-hydroxystyrenemethacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers.

Alkali-soluble resins comprising units of the following formula (2) or (2') are especially preferred.

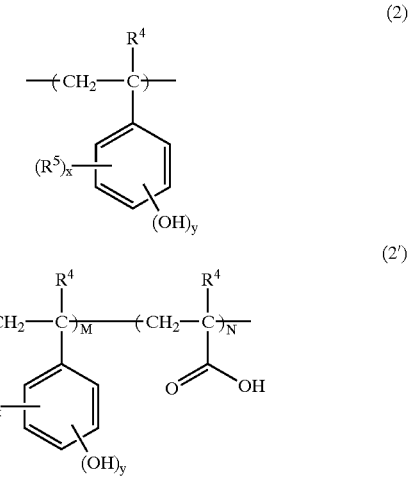

Herein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, and M and N are positive integers, satisfying $0 < N/(M+N) \leq 0.5$.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

To impart a certain function, suitable substituent groups may be introduced into some of the phenolic hydroxyl and carboxyl groups on the acid labile group-protected polymer. Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxoranyl, 4-methyl-2-oxo-4-oxanyl, methyl, ethyl, n-propyl, isopropyl, n-butyl, sec-butyl, acetyl, pivaloyl, adamantyl, isobornyl, and cyclohexyl. It is also possible to introduce acid-decomposable substituent groups such as t-butoxycarbonyl and relatively acid-undecomposable substituent groups such as t-butyl and t-butoxycarbonylmethyl.

Also contained in the negative resist composition is (I) an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition comprising the onium salt according to the invention. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred acid crosslinking agents are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the resist composition, an appropriate amount of the acid crosslinking agent is about 1 to 25 parts, and especially about 5 to 15 parts by weight per 100 parts by weight of the solids in the composition. The acid crosslinking agents may be used alone or in admixture of two or more.

In the chemical amplification type, negative working, resist composition, (J) an alkali-soluble compound having a molecular weight of up to 2,500 may be blended. The compound should preferably have at least two phenol and/or carboxyl groups. Illustrative, non-limiting, examples include cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The addition amount is 0 to 20 parts, preferably 2 to 10 parts by weight per 100 parts by weight of the solids in the composition although it is not critical.

In the resist composition according to the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products K.K.), Megaface F171, F172 and F173 (Dai-Nippon Ink & Chemicals K.K.), Florade FC430 and FC431 (Sumitomo 3M K.K.), Aashiguard AG710, Surflon S-381, S-382, SC101, SC102, SC103, SC104, SC105, SC106, Surfynol E1004, KH-10, KH-20, KH-30 and KH-40 (Asahi Glass K.K.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). Inter alia, FC430, Surflon S-381 and Surfynol E1004 are preferred. These surfactants may be used alone or in admixture.

In the resist composition according to the invention, the surfactant is preferably formulated in an amount of up to 2 parts, and especially up to 1 part by weight, per 100 parts by weight of the solids in the resist composition.

In the resist composition according to the invention, a UV absorber may be added. Exemplary UV absorbers are fused polycyclic hydrocarbon derivatives such as pentalene, indene, naphthalene, azulene, heptalene, biphenylene, indacene, fluorene, phenalene, phenanthrene, anthracene, fluoranthene, acephenanthrylene, aceanthrylene, triphenylene, pyrene, chrysene, pleiadene, picene, perylene, pentaphene, pentacene, benzophenanthrene, anthraquinone, anthrone, benzanthrone, 2,7-dimethoxynaphthalene, 2-ethyl-9,10-dimethoxyanthracene, 9,10-dimethylanthracene, 9-ethoxyanthracene, 1,2- naphthoquinone, 9-fluorene, and compounds of the following formulae (D1) and (D2); fused heterocyclic derivatives such as thioxanthen-9-one, thianthrene, and dibenzothiophene; benzophenone derivatives such as 2,3,4-trihydroxybenzophenone, 2,3,4,4'-tetrahydroxybenzophenone, 2,4-dihydroxybenzophenone, 3,5-dihydroxybenzophenone, 4,4'-dihydroxybenzophenone, and 4,4'-bis(dimethylamino)benzophenone; squalic acid derivatives such as squalic acid and dimethyl squalate; diaryl sulfoxide derivatives such as bis(4-hydroxyphenyl) sulfoxide, bis(4-tert-butoxyphenyl) sulfoxide, bis(4-tert-butoxycarbonyloxyphenyl) sulfoxide, and bis[4-(1-ethoxyethoxy)phenyl] sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl] sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

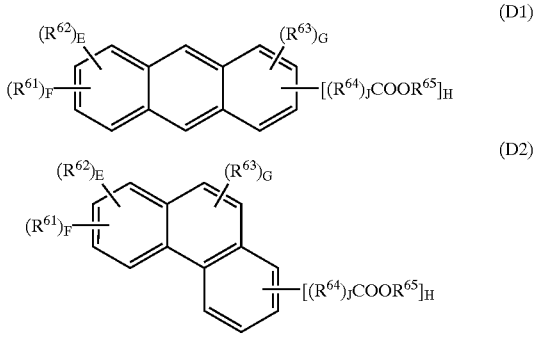

Herein, $R^{61}$ to $R^{63}$ are independently hydrogen or a straight or branched alkyl, straight or branched alkoxy, straight or branched alkoxyalkyl, straight or branched alkenyl or aryl group. $R^{64}$ is a substituted or unsubstituted divalent aliphatic hydrocarbon group which may contain an oxygen atom, a substituted or unsubstituted divalent alicyclic hydrocarbon group which may contain an oxygen atom, a substituted or unsubstituted divalent aromatic hydrocarbon group which may contain an oxygen atom, or an oxygen atom. $R^{65}$ is an acid labile group as described above. Letter J is equal to 0 or 1, E, F and G are 0 or integers of 1 to 9, H is a positive integer of 1 to 10, satisfying E+F+G+H≦10.

An appropriate amount of UV absorber blended is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemical amplification, positive or negative working, resist composition according to the invention.

The composition is applied onto a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 μm thick. With a mask having a desired pattern placed above the resist film, the resist film is then exposed to actinic radiation, preferably having an exposure wavelength of up to 300 nm, such as UV, deep-UV, electron beams, x-rays, excimer laser light, γ-rays and synchrotron radiation in an exposure dose of about 1 to 200 $mJ/cm^2$, preferably about 10 to 100 $mJ/cm^2$. The film is further baked on a hot plate at 60 to 150° C. for 1 to 5 minutes, preferably 80 to 120° C. for 1 to 3 minutes (post-exposure baking=PEB).

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dipping, puddling or spraying. In this way, a desired resist pattern is formed on the substrate. It is appreciated that the resist composition of the invention is best suited for micro-patterning using such actinic radiation as deep UV with a wavelength of 254 to 193 nm, electron beams, x-rays, excimer laser light, γ-rays and synchrotron radiation. With any of the above-described parameters outside the above-described range, the process may sometimes fail to produce the desired pattern.

EXAMPLE

Examples of the invention are given below by way of illustration and not by way of limitation.

Synthesis Example 1

Synthesis of 4-Phenylmethylbenzenesulfonic Acid

To 33.6 g (0.2 mol) of diphenylmethane in 100 g of dichloromethane at room temperature, 23.4 g (0.2 mol) of chlorosulfonic acid was added dropwise. The solution was ripened for 2 hours, whereupon 50 g of water was added. This reaction mixture was used in the subsequent reaction without isolation.

Synthesis Example 2

Synthesis of Triphenylsulfonium Chloride

In 160 g of dichloromethane was dissolved 16.1 g (0.08 mol) of diphenyl sulfoxide. With stirring under ice cooling, 26 g (0.24 mol) of trimethylsilyl chloride was added dropwise at such a rate that the temperature might not exceed 20° C. The reaction solution was ripened at the temperature for 30 minutes. Then, the Grignard reagent which was separately prepared from 5.8 g (0.24 mol) of metallic magnesium, 27 g (0.24 mol) of chlorobenzene and 67.2 g of THF was added dropwise at such a rate that the temperature might not exceed 20° C. The reaction solution was ripened for one hour. Below 20° C., 5 g of water was added to the reaction solution for terminating the reaction. Further, 60 g of water, 4 g of 12N hydrochloric acid and 100 g of diethyl ether were added to the solution.

The aqueous layer was separated and washed with 30 g of diethyl ether, obtaining an aqueous solution of triphenylsulfonium chloride. This aqueous solution was subject to the subsequent reaction without further purification.

Synthesis Example 3

Synthesis of Triphenylsulfonium 4-Phenylmethylbenzenesulfonate

The 4-phenylmethylbenzenesulfonic acid crude product obtained in Synthesis Example 1 was added to the aqueous triphenylsulfonium chloride solution obtained in Synthesis Example 2 and 90 g of dichloromethane, which was stirred for one hour at room temperature. The organic layer was separated, washed with 100 g of water, and evaporated in vacuum. The residue, 27 g, was purified by silica gel column chromatography (eluent, dichloromethane/methanol), obtaining the end product, triphenylsulfonium 4-phenylmethylbenzenesulfonate. It was 21 g (yield 52%) of an oily matter containing a minor amount of solvents (methanol, etc.).

The thus obtained triphenylsulfonium 4-phenylmethylbenzenesulfonate was analyzed by nuclear magnetic resonance (NMR) spectroscopy and infrared (IR) absorption spectroscopy, with the results shown below.

$^1$H-NMR: CDCl$_3$, ppm;

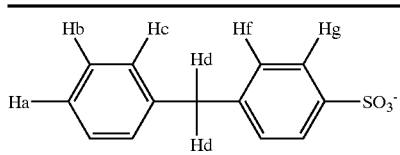

| (1) Ha, Hb, Hc, Hf | 6.99–7.18 | multiplet 7H |
|---|---|---|
| (2) Hd | 3.84 | singlet 2H |
| (3) Hg + Hh | 7.48–7.74 | multiplet 17H |

IR: cm$^{-1}$; 1600, 1477, 1448, 1403, 1218, 1120, 1066, 1033, 1012.

Synthesis Example 4

Synthesis of 4-(Diphenylmethyl)benzenesulfonic Acid

The end product was synthesized as in Synthesis Example 1 except that triphenylmethane was used instead of the diphenylmethane and the amount of dichlorometahne was tripled. The reaction mixture was used in the subsequent reaction without isolation.

Synthesis Example 5

Synthesis of Triphenylsulfonium 4-Diphenylmethylbenzenesulfonate

The end product was synthesized as in Synthesis Example 3 except that 4-diphenylmethylbenzenesulfonic acid prepared in Synthesis Example 4 was used instead of the phenylmethylbenzenesulfonic acid in Synthesis Example 3. The thus obtained triphenylsulfonium 4-diphenylmethylbenzenesulfonate was analyzed by NMR and IR spectroscopy, with the results shown below.

$^1$H-NMR: CDCl$_3$, ppm;

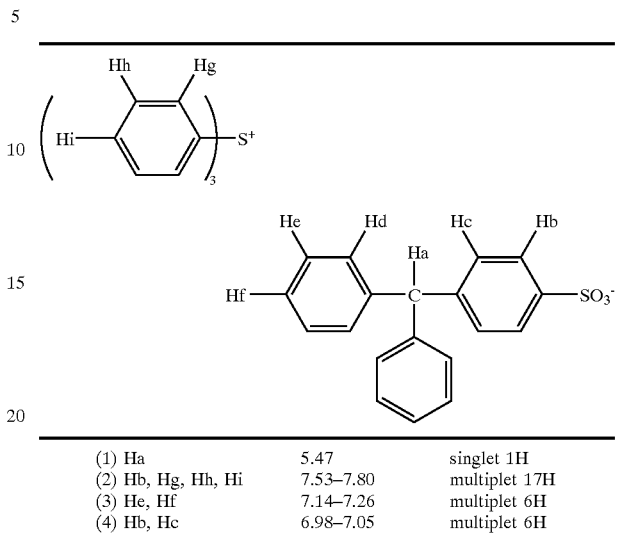

| (1) Ha | 5.47 | singlet 1H |
|---|---|---|
| (2) Hb, Hg, Hh, Hi | 7.53–7.80 | multiplet 17H |
| (3) He, Hf | 7.14–7.26 | multiplet 6H |
| (4) Hb, Hc | 6.98–7.05 | multiplet 6H |

IR: cm$^{-1}$; 1600, 1492, 1475, 1446, 1319, 1203, 1122, 1074, 1064, 1033, 1012, 921, 877, 837, 809, 746, 709, 684.

Synthesis Example 6

Synthesis of 4-(1'-Methyl-1'-phenyl)ethylbenzenesulfonic Acid

The end product was synthesized as in Synthesis Example 1 except that 2,2-diphenylpropane was used instead of the diphenylmethane.

Synthesis Example 7

Synthesis of 4-tert-Butylphenyldiphenylsulfonium Chloride

The end product was synthesized as in Synthesis Example 2 except that 4-tert-butylchlorobenzene was used instead of the chlorobenzene and the amount of water used for extraction was increased.

Synthesis Example 8

Synthesis of 4-tert-Butoxyphenyldiphenylsulfonium Chloride

The end product was synthesized as in Synthesis Example 2 except that 4-tert-butoxychlorobenzene was used instead of the chlorobenzene, dichloromethane containing 5 wt % triethylamine was used as a solvent, and the amount of water used for extraction was increased.

Synthesis Example 9

Synthesis of bis(4-tert-Butylphenyl)iodonium Hydrogen Sulfate

While a mixture of 168 g (1.0 mol) of tert-butylbenzene, 107 g (0.5 mol) of potassium iodate and 100 g of acetic anhydride was stirred under ice cooling, a mixture of 70 g of acetic anhydride and 190 g of conc. sulfuric acid was added dropwise at such a rate that the temperature might not exceed 30° C. The reaction solution was ripened for 3 hours at room temperature. The solution was ice cooled again and 500 g of water was added dropwise for terminating the reaction. The reaction solution was extracted with 800 g of dichloromethane. Sodium hydrogen sulfite, 12 g, was added to the organic layer for decoloring. The organic layer was washed three times with 500 g of water. The washed organic layer was concentrated in vacuum, obtaining the crude end product. This product was subject to the subsequent reaction without further purification.

Synthesis Example 10

Synthesis of bis(4-tert-Butylphenyl)iodonium 4-phenyl-methylbenzenesulfonate

The end product was obtained as in Synthesis Example 3 except that the one-fifth amount of bis(4-tert-butylphenyl)iodonium hydrogen sulfate obtained in Synthesis Example 9 was used instead of the triphenylsulfonium chloride in Synthesis Example 3, and 100 g of water was further added.

Synthesis Example 11

Synthesis of 4-tert-Butylphenyldiphenylsulfonium 4-Diphenylmethylbenzenesulfonate The end product was obtained as in Synthesis Example 5 except that 4-tert-butylphenyldiphenylsulfonium chloride was used instead of the triphenylsulfonium chloride in Synthesis Example 5.

Synthesis Example 12

Synthesis of 4-tert-Butoxyphenyldiphenylsulfonium 4-Diphenylmethylbenzenesulfonate The end product was obtained as in Synthesis Example 11 except that 4-tert-butoxyphenyldiphenylsulfonium chloride was used instead of the 4-tert-butylphenyldiphenylsulfonium chloride in Synthesis Example 11.

Synthesis Example 13

Synthesis of Triphenylsulfonium 4-(1'-Methyl-1'-phenyl)ethylbenzenesulfonate

The end product was obtained as in Synthesis Example 3 except that 4-(1-methyl-1'-phenyl)ethylbenzenesulfonic acid obtained in Synthesis Example 6 was used instead of the phenylmethylbenzenesulfonic acid in Synthesis Example 3.

Examples 1–21 and Comparative Examples 1–3

Resist materials were formulated in accordance with the formulation shown in Tables 1 to 3. The components used are shown below.

Polymer A: poly(p-hydroxystyrene) in which hydroxyl groups are protected with 15 mol % of 1-ethoxyethyl groups and 15 mol % of tert-butoxycarbonyl groups, having a weight average molecular weight of 12,000.
Polymer B: poly(p-hydroxystyrene) in which hydroxyl groups are protected with 10 mol % of 1-ethoxyethyl groups and 15 mol % of tert-butoxycarbonyl groups, having a weight average molecular weight of 11,000.
Polymer C: poly(p-hydroxystyrene) in which hydroxyl groups are protected with 15 mol % of 1-ethoxyethyl groups and 10 mol % of tert-butoxycarbonyl groups, having a weight average molecular weight of 11,000.
Polymer D: poly(p-hydroxystyrene) in which hydroxyl groups are protected with 10 mol % of 1-ethoxyethyl groups and 10 mol % of tert-butoxycarbonyl groups, and crosslinked with 2 mol % of 1,2-propanediol divinyl ether, having a weight average molecular weight of 15,000.
Polymer E: poly(p-hydroxystyrene) in which hydroxyl groups are protected with 30 mol % of 1-ethoxyethyl groups, having a weight average molecular weight of 12,000.
Polymer F: poly(p-hydroxystyrene) in which hydroxyl groups are protected with 25 mol % of 1-ethoxyethyl groups and crosslinked with 3 mol % of 1,2-propanediol divinyl ether, having a weight average molecular weight of 13,000.
Polymer G: p-hydroxystyrene-1-ethylcyclopentyl methacrylate copolymer having a compositional ratio (molar ratio) of 70:30 and a weight average molecular weight of 11,000.
Polymer H: p-hydroxystyrene-1-ethylcyclopentyl acrylate copolymer having a compositional ratio (molar ratio) of 65:35 and a weight average molecular weight of 14,000.
Polymer I: the same as Polymer G. but further containing 5% by weight of styrene and having a weight average molecular weight of 12,000.
Polymer J: p-hydroxystyrene-1-ethylcyclopentyl methacrylate copolymer having a compositional ratio (molar ratio) of 70:30 in which hydroxyl groups on p-hydroxystyrene are crosslinked with 1 mol % of 1,4-butanediol divinyl ether, and having a weight average molecular weight of 15,000.
Polymer K: p-hydroxystyrene-1-ethylcyclopentyl methacrylate copolymer having a compositional ratio (molar ratio) of 80:20 in which hydroxyl groups on p-hydroxystyrene are protected with 8 mol % of tert-butoxycarbonyl groups, and having a weight average molecular weight of 13,000.
Polymer L: poly(p-hydroxystyrene) in which hydrogen atoms of hydroxyl groups are replaced by 8 mol % of acetyl groups, having a weight average molecular weight of 8,000.
PAG1: triphenylsulfonium 4-phenylmethylbenzenesulfonate
PAG2: (tert-butoxyphenyl)diphenylsulfonium 4-diphenylmethylbenzenesulfonate
PAG3: bis(4-tert-butylphenyliodonium) 4-phenylmethylbenzenesulfonate
PAG4: (4-tert-butoxyphenyl)diphenylsulfonium p-toluenesulfonate
PAG5: (4-tert-butoxyphenyl)diphenylsulfonium 10-camphorsulfonate
PAG6: triphenylsulfonium trifluoromethanesulfonate
PAG7: bis(cyclohexylsulfonyl)diazomethane
PAG8: bis(2,4-dimethylphenylsulfonyl)diazomethane
PAG9: N-10-camphorsulfonyloxysuccinimide
Crosslinker A: 1,3,5,7-tetramethoxymethylglycoluril
Dissolution inhibitor A: bis(4-(21-tetrahydropyranyloxy)phenyl)methane
Basic compound A: tri-n-butylamine
Basic compound B: tris(2-methoxyethyl)amine
Organic acid derivative A: 4,4-bis(4'-hydroxyphenyl)valeric acid
Organic acid derivative B: salicylic acid
Surfactant A: FC-430 (Sumitomo 3M K.K.)
Surfactant B: Surflon S-381 (Asahi Glass K.K.)
Solvent A: propylene glycol methyl ether acetate
Solvent B: ethyl lactate
The resist materials thus obtained were each filtered through a 0.2-μm Teflon filter, thereby giving resist solutions. These resist solutions were spin-coated onto silicon wafers, then baked at 100° C. for 90 seconds on a hot plate to give resist films having a thickness of 0.6 μm. The resist films were exposed using an excimer laser stepper NSR2005EX (Nikon K.K., NA 0.5), then baked (PEB) at 110° C. for 90 seconds, and developed with a solution of 2.38% tetramethylammonium hydroxide in water, thereby giving positive patterns (Examples 1 to 20 and Comparative Examples 1–3) or negative patterns (Example 21).

The resulting resist patterns were evaluated as described below.

Resist Pattern Evaluation

Provided that the exposure dose which provides a 1:1 resolution at the top and bottom of a 0.24-μm line-and-space pattern was the optimum exposure dose (sensitivity Eop), the minimum line width of a line-and-space pattern which was ascertained separate at this dose was the resolution of a test resist. The shape in cross section of the resolved resist pattern was examined under a scanning electron microscope.

The PED stability of a resist was evaluated by effecting post-exposure bake (PEB) after 24 hours of holding from exposure at the optimum dose and determining a variation in line width (or groove width for the negative resist). The less the variation, the greater is the PED stability.

The results of resist pattern evaluation are shown in Table 4.

Other Evaluation

The solubility of resist material in a solvent mixture was examined by visual observation and in terms of clogging upon filtration.

With respect to the applicability of a resist solution, uneven coating was visually observed. Additionally, using a film gage Clean Track Mark 8 (Tokyo Electron K.K.), the thickness of a resist film on a common wafer was measured at different positions, based on which a variation from the desired coating thickness (0.6 μm) was calculated. The applicability was rated "good" when the variation was within 0.5% (that is, within 0.003 μm), "unacceptable" when the variation was from more than 0.5% to 1%, and "poor" when the variation was more than 1%.

Storage stability was judged in terms of foreign matter precipitation or sensitivity change during aging. After the resist solution was aged for 100 days at the longest, the number of particles of greater than 0.3 μm per ml of the resist solution was counted by means of a particle counter KL-20A (Rion K.K.), and the foreign matter precipitation was determined "good" when the number of particles is not more than 5. Also, the sensitivity change was rated "good" when a change with time of sensitivity (Eop) was within 5% from that immediately after preparation, and "poor" when the change is more than 5%.

Defect appearing on the developed pattern was observed under a scanning electron microscope (TDSEM) model S-7280H (Hitachi K.K.). The resist film was rated "good" when the number of defect (particles) was up to 10 per 100 μm$^2$, "unacceptable" when from 11 to 15, and "poor" when more than 15.

Defect (residue) left after resist stripping was examined using a surface scanner Surf-Scan 6220 (Tencol Instruments). A resist-coated 8-inch wafer was subjected to entire exposure rather than patterned exposure, processed in a conventional manner, and developed with a 2.38% TMAH solution before the resist film was peeled off (only the resist film in the exposed area was stripped). After the resist film was stripped, the wafer was examined and rated "good" when the number of defect of greater than 0.20 μm was up to 100, "unacceptable" when from 101 to 150, and "poor" when more than 150.

The results are shown in Table 5.

TABLE 1

| Composition (pbw) | E1 | E2 | E3 | E4 | E5 | E6 | E7 | E8 | E9 | E10 | E11 | E12 |
|---|---|---|---|---|---|---|---|---|---|---|---|---|
| Polymer A | 80 | 40 | | | 40 | | | | | | | |
| Polymer B | | | 60 | | | | 20 | | | | | |
| Polymer C | | | | 20 | | | | | 60 | | | |
| Polymer D | | | | | 40 | 60 | | 40 | 20 | | | |
| Polymer E | | 40 | | 60 | | 20 | | | | | | |
| Polymer F | | | 20 | | | | 60 | 40 | | | | |
| Polymer G | | | | | | | | | | 80 | | 40 |
| Polymer H | | | | | | | | | | | 80 | |
| Polymer I | | | | | | | | | | | | 40 |
| Polymer J | | | | | | | | | | | | |
| Polymer K | | | | | | | | | | | | |
| Polymer L | | | | | | | | | | | | |
| PAG1 | 2 | | 2 | | | 2 | | 1 | 1 | | | 2 |
| PAG2 | | 2 | | | 2 | | 2 | 1 | | | 2 | |
| PAG3 | | | | 2 | | | | | | 1 | 2 | |
| PAG4 | | | 0.5 | | | | | | | | | |
| PAG5 | | | | | 1 | | | | | | | 1 |
| PAG6 | | | | | | | | | | | | |
| PAG7 | | | | | | | 1 | | | | | |
| PAG8 | | | | | | | | | | | 0.5 | |
| PAG9 | | | | | | | | | 1 | | | |
| Crosslinker A | | | | | | | | | | | | |
| Dissolution inhibitor A | | | | | | | | | | | | |
| Basic compound A | | 0.125 | | | 0.125 | 0.125 | 0.125 | | 0.125 | | | |

TABLE 1-continued

| Composition (pbw) | E1 | E2 | E3 | E4 | E5 | E6 | E7 | E8 | E9 | E10 | E11 | E12 |
|---|---|---|---|---|---|---|---|---|---|---|---|---|
| Basic compound B | 0.125 | | 0.125 | 0.125 | | | | 0.125 | | 0.125 | 0.125 | 0.125 |
| Organic acid derivative A | 1 | | | 1 | 1 | 1 | | | 1 | | 1 | |
| Organic acid derivative B | | 1 | 1 | | | | 1 | 1 | | 1 | | 1 |
| Surfactant A | 0.25 | | | | 0.25 | | 0.25 | | 0.125 | 0.25 | | |
| Surfactant B | | 0.25 | 0.25 | 0.25 | | 0.25 | | 0.25 | 0.125 | | 0.25 | 0.25 |
| Solvent A | 280 | 280 | 280 | 388 | 280 | 280 | 280 | 280 | 388 | 388 | 280 | 280 |
| Solvent B | 105 | 105 | 105 | | 105 | 105 | 105 | 105 | | | 105 | 105 |

TABLE 2

| Composition (pbw) | E13 | E14 | E15 | E16 | E17 | E18 | E19 | E20 | E21 |
|---|---|---|---|---|---|---|---|---|---|
| Polymer A | | | 60 | | | | 40 | | |
| Polymer B | | | | | | | | | |
| Polymer C | | | | | | | | | |
| Polymer D | | | | | | | | | |
| Polymer E | | | | | | | | | |
| Polymer F | | | | | | 60 | | | |
| Polymer G | | 20 | | | | | | | |
| Polymer H | | | | 60 | | 20 | 40 | 20 | |
| Polymer I | | | | | 20 | | | | |
| Polymer J | 80 | | | | 60 | | | | |
| Polymer K | | 80 | | 20 | | | | 60 | |
| Polymer L | | | | | | | | | 80 |
| PAG1 | | 1 | | | 2 | | 2 | 1 | |
| PAG2 | 2 | | 2 | | | 2 | | | |
| PAG3 | | 1 | | 2 | | | | 1 | 2 |
| PAG4 | 0.5 | | | | | | | | |
| PAG5 | | | 0.5 | 1 | | | | | |
| PAG6 | | | | | | 0.1 | | | |
| PAG7 | | | | | | | | | |
| PAG8 | | | | | | | | | |
| PAG9 | | | | | 1 | 1 | | | 1 |
| Crosslinker A | | | | | | | | | 10 |
| Dissolution inhibitor A | | | 2 | | | | 2 | | |
| Basic compound A | 0.125 | 0.125 | | | 0.063 | | | 0.125 | 0.125 |
| Basic compound B | | | 0.125 | 0.125 | 0.063 | 0.125 | 0.125 | | |
| Organic acid derivative A | | | 1 | | | 1 | | 1 | 1 |
| Organic acid derivative B | 1 | 1 | | 1 | 1 | | 1 | | |
| Surfactant A | 0.25 | 0.25 | | 0.25 | | | 0.25 | 0.25 | |
| Surfactant B | | | 0.25 | | 0.25 | 0.25 | | | 0.25 |
| Solvent A | 280 | 280 | 280 | 388 | 280 | 280 | 280 | 388 | 388 |
| Solvent B | 105 | 105 | 105 | | 105 | 105 | 105 | | |

TABLE 3

| Composition (pbw) | CE1 | CE2 | CE3 |
|---|---|---|---|
| Polymer A | 80 | | |
| Polymer D | | 80 | |
| Polymer G | | | 80 |
| PAG4 | | | 1 |
| PAG8 | 2 | | 2 |
| PAG9 | 1 | 2 | |
| Basic compound A | 0.125 | 0.125 | |
| Basic compound B | | | 0.125 |
| Organic acid derivative A | 1 | | |
| Organic acid derivative B | | | |
| Surfactant A | | 0.25 | 0.25 |
| Surfactant B | | | 0.25 |
| Solvent A | 388 | 388 | 388 |

TABLE 4

| | Sensitivity (mJ/cm$^2$) | Resolution ($\mu$m) | Profile | 24 hr PED dimensional stability (nm) |
|---|---|---|---|---|
| E1 | 29 | 0.20 | rectangular | −8 |
| E2 | 30 | 0.21 | rectangular | −5 |
| E3 | 26 | 0.20 | rectangular | −10 |

TABLE 4-continued

| | Sensitivity (mJ/cm²) | Resolution (μm) | Profile | 24 hr PED dimensional stability (nm) |
|---|---|---|---|---|
| E4 | 24 | 0.19 | rectangular | −10 |
| E5 | 28 | 0.20 | rectangular | −6 |
| E6 | 24 | 0.20 | rectangular | −9 |
| E7 | 25 | 0.21 | rectangular | −7 |
| E8 | 28 | 0.20 | rectangular | −6 |
| E9 | 30 | 0.20 | rectangular | −3 |
| E10 | 28 | 0.19 | rectangular | 5 |
| E11 | 26 | 0.19 | rectangular | 6 |
| E12 | 30 | 0.20 | rectangular | 8 |
| E13 | 28 | 0.19 | rectangular | 3 |
| E14 | 32 | 0.21 | rectangular | 12 |
| E15 | 30 | 0.20 | rectangular | −5 |
| E16 | 26 | 0.21 | rectangular | 5 |
| E17 | 30 | 0.20 | rectangular | 5 |
| E18 | 28 | 0.20 | rectangular | −5 |
| E19 | 28 | 0.20 | rectangular | −3 |
| E20 | 30 | 0.21 | rectangular | 3 |
| E21 | 35 | 0.24 | rectangular | −10 |
| CE1 | 36 | 0.22 | forward tapered | −30 |
| CE2 | 34 | 0.24 | forward tapered | −30 |
| CE3 | 34 | 0.24 | rounded head | 30 |

TABLE 5

| | Dissolution | Application | 100 day storage stability | Debris after development (patterning) | Defect after stripping |
|---|---|---|---|---|---|
| E1 | good | good | good | good | good |
| E2 | good | good | good | good | good |
| E3 | good | good | good | good | good |
| E4 | good | good | good | good | good |
| E5 | good | good | good | good | good |
| E6 | good | good | good | good | good |
| E7 | good | good | good | good | good |
| E8 | good | good | good | good | good |
| E9 | good | good | good | good | good |
| E10 | good | good | good | good | good |
| E11 | good | good | good | good | good |
| E12 | good | good | good | good | good |
| E13 | good | good | good | good | good |
| E14 | good | good | good | good | good |
| E15 | good | good | good | good | good |
| E16 | good | good | good | good | good |
| E17 | good | good | good | good | good |
| E18 | good | good | good | good | good |
| E19 | good | good | good | good | good |
| E20 | good | good | good | good | good |
| E21 | good | good | good | good | good |
| CE1 | unacceptable | good | <30 days (sensitivity changed) | poor | Unacceptable |
| CE2 | good | good | <30 days (sensitivity changed) | good | good |
| CE3 | unacceptable | good | good | poor | Unacceptable |

There have been described specific onium salts having a substituted phenylmethylbenzenesulfonate anion. Chemical amplification type resist compositions comprising the onium salts as the photoacid generator have many advantages including improved resolution, improved focus latitude, minimized line width variation or shape degradation even on long-term PED, minimized defect left after coating, development and stripping, and improved pattern profile after development. Because of high resolution, the compositions are suited for microfabrication, especially by deep UV lithography.

Japanese Patent Application No. 11-285143 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An onium salt of the following general formula (1):

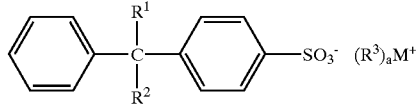

(1)

wherein R¹ is hydrogen or a straight, branched or cyclic alkyl group of 1 to 6 carbon atoms, R² is hydrogen, a straight, branched or cyclic alkyl group of 1 to 6 carbon atoms or phenyl group, R³ which may be the same or different is a substituted or unsubstituted, straight, branched or cyclic alkyl group of 1 to 10 carbon atoms or substituted or unsubstituted aryl group of 6 to 14 carbon atoms, M is a sulfur or iodine atom, and "a" is equal to 3 when M is sulfur and equal to 2 when M is iodine.

2. A sulfonium salt of the following general formula (1a):

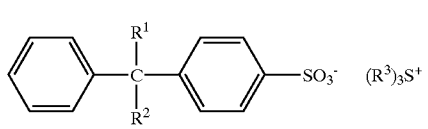

(1a)

wherein R¹, R² and R³ are as defined above.

3. A sulfonium salt of the following general formula (1a'):

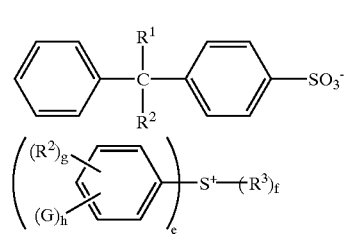

(1a')

wherein R¹, R² and R³ are as defined above, G is an acid labile group having an oxygen atom attached thereto or R²O— or (R²)₂N—, g is an integer of 0 to 4, h is an integer of 1 to 5, g+h=5, e is an integer of 1 to 3, f is an integer of 0 to 2, and e+f=3.

4. The sulfonium salt of claim 3 wherein the acid labile group is selected from the group consisting of tert-butoxy group, tert-amyloxy group, tert-butoxycarbonyloxy group, tert-butoxycarbonylmethyloxy group, 1-ethoxyethoxy group, tetrahydropyranyloxy group, tetrahydrofuranyloxy group, trimethylsilyloxy group and 1-ethylcyclopentyloxy group.

5. A iodonium salt of the following general formula (1b):

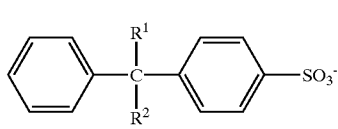

(1b)

-continued

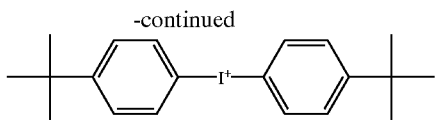

wherein $R^1$ and $R^2$ are as defined above.

6. A photoacid generator for a chemical amplification type resist composition comprising an onium salt of claim 1.

7. A chemical amplification type resist composition comprising (A) a resin which changes its solubility in an alkaline developer under the action of an acid, and (B) the photoacid generator of claim 6 which generates an acid upon exposure to radiation.

8. The resist composition of claim 7 wherein the resin (A) has such substituent groups having C—O—C linkages that the solubility in an alkaline developer changes as a result of cleavage of the C—O—C linkages under the action of an acid.

9. The resist composition of claim 7 wherein the resin (A) is a polymer containing phenolic hydroxyl groups in which hydrogen atoms of the phenolic hydroxyl groups are substituted by acid labile groups of at least one type in a proportion of more than 0 mol % to 80 mol %, on the average, of the entire hydrogen atoms of the phenolic hydroxyl groups, said polymer having a weight average molecular weight of 3,000 to 100,000.

10. The resist composition of claim 7 wherein the resin (A) is a polymer comprising recurring units represented by the following general formula (2a):

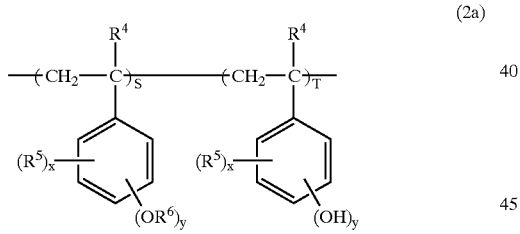

wherein $R^4$ is hydrogen or methyl, $R^5$ is a straight, branched or cyclic alkyl group of 1 to 8 carbon atoms, $R^6$ is an acid labile group, $R^6$ groups may be the same or different when y is at least 2, x is 0 or a positive integer, satisfying $x+y \leq 5$, and S and T are positive integers, satisfying $0<S/(S+T)\leq 0.8$, wherein the units having the acid labile groups are present in a proportion of more than 0 mol % to 80 mol %, on the average, based on the entire polymer, and the polymer has a weight average molecular weight of 3,000 to 100,000.

11. The resist composition of claim 10 wherein the resin (A) is the polymer of formula (2a) or (2a') in which the hydrogen atoms of the remaining phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3a) or (3b):

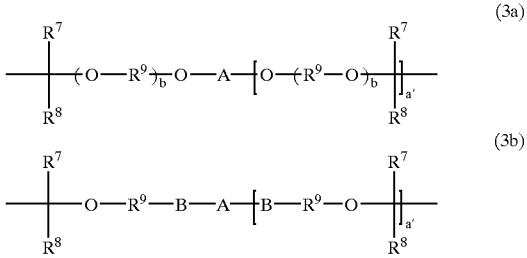

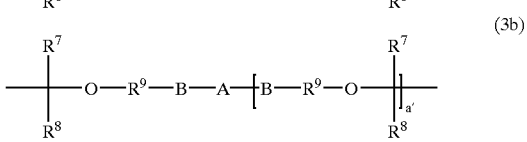

wherein each of $R^7$ and $R^8$ is hydrogen or a straight, branched or cyclic alkyl group of 1 to 8 carbon atoms, or $R^7$ and $R^6$, taken together, may form a ring, and each of $R^7$ and $R^8$ is a straight or branched alkylene group of 1 to 8 carbon atoms when they form a ring, $R^9$ is a straight, branched or cyclic alkylene group of 1 to 10 carbon atoms, letter a' is an integer of 1 to 7, letter b is 0 or an integer of 1 to 10, A is an (a'+1)-valent aliphatic or alicyclic saturated hydrocarbon group, aromatic hydrocarbon group or heterocyclic group of 1 to 50 carbon atoms, which may be separated by a hetero atom and in which some of the hydrogen atoms attached to carbon atoms may be replaced by hydroxyl, carboxyl, carbonyl or halogen, B is —CO—O—, —NHCO—O— or —NHCONH—.

12. The resist composition of claim 10 wherein said acid labile groups are groups of the following general formulae (4) to (7), tertiary alkyl groups of 4 to 20 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms,

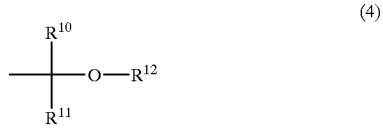

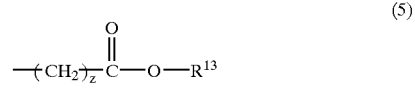

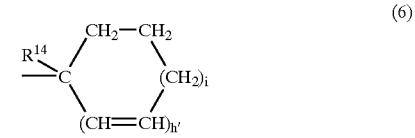

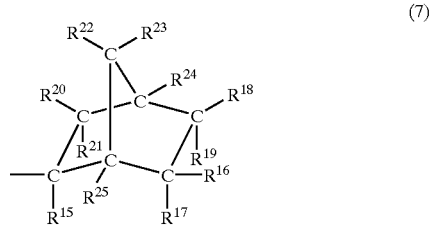

wherein $R^{10}$ and $R^{11}$ are independently hydrogen or straight, branched or cyclic alkyl groups of 1 to 18 carbon atoms, $R^{12}$ is a monovalent hydrocarbon group of 1 to 18 carbon atoms which may have a hetero atom, or $R^{10}$ and $R^{11}$, $R^{10}$ and $R^{12}$, or $R^{11}$ and $R^{12}$, taken together, may form a ring, with the proviso that each of $R^{10}$, $R^{11}$ and $R^{12}$ is a straight or branched alkylene group of 1 to 18 carbon atoms when they form a ring, $R^{13}$ is a tertiary alkyl group of 4 to 20 carbon atoms, a trialkylsilyl group whose alkyl groups each have 1 to 6 carbon atoms, an oxoalkyl group of 4 to 20 carbon atoms or a group of formula (4), and letter z is an integer of 0 to 6, $R^{14}$ is a straight, branched or cyclic alkyl group of 1 to 8 carbon atoms or substituted or unsubstituted aryl group of 6 to 20 carbon atoms, h' is equal to 0 or 1, i is equal to 0, 1, 2 or 3, satisfying 2h'+i=2 or 3, $R^{15}$ is a straight, branched or cyclic alkyl group of 1 to 8 carbon atoms or substituted or unsubstituted aryl group of 6 to 20 carbon atoms, $R^{16}$ to $R^{25}$ are independently hydrogen or monovalent hydrocarbon groups of 1 to 15 carbon atoms which may contain a hetero atom, or $R^{16}$ to $R^{25}$, taken together, may form a ring, with the proviso that they are divalent hydrocarbon groups of 1 to 15 carbon atoms which may contain a hetero atom when they form a ring, or two of $R^{16}$ to $R^{25}$ which are attached to adjacent carbon atoms may directly bond together to form a double bond.

13. The resist composition of claim 7 wherein the resin (A) is a polymer comprising recurring units represented by the following general formula (2a'):

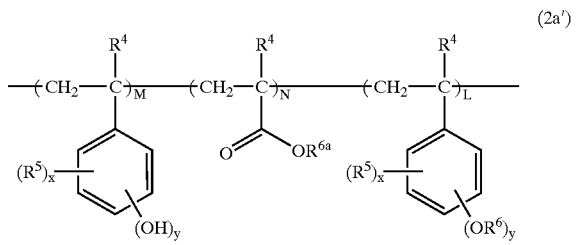

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, $R^{6a}$ being at least partially an acid labile group, x is 0 or a positive integer, y is a positive integer, satisfying x+y≦5, the $R^6$ groups may be the same or different when y is at least 2, M and N are positive integers, L is 0 or a positive integer, satisfying 0<N/(M+N)≦0.5 and 0<(N+L)/(M+N+L)≦0.8, wherein the units of acrylate and methacrylate are contained in the polymer in a proportion of more than 0 mol % to 50 mol % on the average, the unit having the acid labile groups are present in a proportion of more than 0 mol % to 80 mol %, on the average, based on the entire polymer, and the polymer has a weight average molecular weight of 3,000 to 100,000.

14. The resist composition of claim 7 further comprising
    (D) a basic compound.
15. The resist composition of claim 7 further comprising
    (E) a carboxyl group-containing compound.
16. The resist composition of claim 7 further comprising a propylene glycol alkyl ether acetate, an alkyl lactate or a mixture thereof as a solvent.
17. A chemical amplification type resist composition comprising
    (A) a resin which changes its solubility in an alkaline developer under the action of an acid,
    (B) the photoacid generator of claim 6 which generates an acid upon exposure to radiation, and
    (C) a compound capable of generating an acid upon exposure to radiation, other than component (B).
18. A process for forming a pattern, comprising the steps of:
    applying the resist composition of claim 7 onto a substrate to form a coating,
    heat treating the coating and exposing the coating to high energy radiation with a wavelength of up to 300 nm or electron beam through a photo-mask,
    optionally heat treating the exposed coating, and developing the coating with a developer.

* * * * *